US 8,585,718 B2

(12) United States Patent
Disch et al.

(10) Patent No.: US 8,585,718 B2
(45) Date of Patent: Nov. 19, 2013

(54) CARTRIDGE WITH A PLURALITY OF C-SHAPED LIGATURE CLIPS

(75) Inventors: Alexander Disch, Freiburg (DE); Rupert Mayenberger, Rielasingen (DE)

(73) Assignee: Aesculap AG, Tuttlingen (DE)

( * ) Notice: Subject to any disclaimer, the term of this patent is extended or adjusted under 35 U.S.C. 154(b) by 102 days.

(21) Appl. No.: 13/218,583

(22) Filed: Aug. 26, 2011

(65) Prior Publication Data

US 2012/0048759 A1 Mar. 1, 2012

Related U.S. Application Data

(63) Continuation of application No. PCT/EP2010/054824, filed on Apr. 13, 2010.

(30) Foreign Application Priority Data

Apr. 24, 2009 (DE) .......................... 10 2009 018 820

(51) Int. Cl.
*A61B 17/128* (2006.01)
(52) U.S. Cl.
USPC .......................................................... 606/143
(58) Field of Classification Search
USPC ........... 606/142–143, 139, 75, 157–158, 219; 206/339; 227/176.1, 177.1, 178.1
See application file for complete search history.

(56) References Cited

U.S. PATENT DOCUMENTS

| 2,758,302 | A | 8/1956 | White |
| 3,777,538 | A | 12/1973 | Weatherly et al. |
| 3,856,016 | A | 12/1974 | Davis |
| 3,954,108 | A | 5/1976 | Davis |
| 4,299,224 | A | 11/1981 | Noiles |
| 4,412,539 | A | 11/1983 | Jarvik |
| 4,430,997 | A | 2/1984 | DiGiovanni et al. |
| 4,478,220 | A | 10/1984 | Di Giovanni et al. |

(Continued)

FOREIGN PATENT DOCUMENTS

| DE | 24 05 390 | 8/1975 |
| DE | 30 21 099 | 12/1980 |

(Continued)

OTHER PUBLICATIONS

Leaflet of Aesculap AG & Co. KG "Titanium Ligature Clips and Applicators", 8 pages, Feb. 2002.

(Continued)

*Primary Examiner* — Julian W Woo
*Assistant Examiner* — Shaun L David
(74) *Attorney, Agent, or Firm* — Lipsitz & McAllister, LLC

(57) ABSTRACT

In order to simplify the structure of the cartridge and reduce the structural size in a cartridge with a plurality of C-shaped ligature clips, with a housing accommodating ligature clips arranged in a row one behind the other and parallel to one another, with a transport element, which can be slid forward and back relative to the housing in the direction of the row and which when sliding forward and back relative to the housing causes at least one ligature clip to advance towards a discharge end of the cartridge, it is proposed that the ligature clips each have two legs connected by means of a bridge section and are divided by a longitudinal slit into two adjacent sections, which are connected to one another in the region of the free ends of the legs, and that the transport element passes through the ligature clips arranged in a row in the space between the two adjacent sections of the ligature clips.

41 Claims, 29 Drawing Sheets

(56) References Cited

U.S. PATENT DOCUMENTS

| | | |
|---|---|---|
| 4,509,518 A | 4/1985 | McGarry et al. |
| 4,512,345 A | 4/1985 | Green |
| 4,854,317 A | 8/1989 | Braun |
| 4,983,176 A | 1/1991 | Cushman et al. |
| 5,047,038 A | 9/1991 | Peters et al. |
| 5,160,339 A | 11/1992 | Chen et al. |
| 5,171,250 A | 12/1992 | Yoon |
| 5,207,692 A | 5/1993 | Kraus et al. |
| 5,217,473 A | 6/1993 | Yoon |
| 5,366,459 A | 11/1994 | Yoon |
| 5,441,509 A | 8/1995 | Vidal et al. |
| 5,527,320 A | 6/1996 | Carruthers et al. |
| D371,390 S | 7/1996 | Johnson |
| 5,609,599 A | 3/1997 | Levin |
| 5,626,585 A | 5/1997 | Mittelstadt et al. |
| 5,665,097 A | 9/1997 | Baker et al. |
| 5,681,330 A | 10/1997 | Hughett et al. |
| 5,700,271 A | 12/1997 | Whitfield et al. |
| 5,725,542 A | 3/1998 | Yoon |
| 5,772,673 A | 6/1998 | Cuny et al. |
| 5,779,720 A | 7/1998 | Walder-Utz et al. |
| 5,788,716 A | 8/1998 | Kobren et al. |
| D401,626 S | 11/1998 | Shyu |
| 5,843,097 A | 12/1998 | Mayenberger et al. |
| 6,015,417 A | 1/2000 | Reynolds, Jr. |
| 6,352,541 B1 | 3/2002 | Kienzle et al. |
| 6,428,548 B1 | 8/2002 | Durgin et al. |
| 6,837,895 B2 | 1/2005 | Mayenberger |
| 7,207,997 B2 | 4/2007 | Shipp et al. |
| 7,572,266 B2 | 8/2009 | Young et al. |
| D600,749 S | 9/2009 | Azman et al. |
| D600,750 S | 9/2009 | Azman et al. |
| 7,678,125 B2 | 3/2010 | Shipp |
| 2002/0099388 A1 | 7/2002 | Mayenberger |
| 2004/0147942 A1 | 7/2004 | Chao |
| 2005/0177177 A1 | 8/2005 | Viola |
| 2006/0212049 A1 | 9/2006 | Mohiuddin |
| 2008/0045981 A1 | 2/2008 | Margolin et al. |
| 2008/0312670 A1 | 12/2008 | Lutze et al. |

FOREIGN PATENT DOCUMENTS

| | | |
|---|---|---|
| DE | 37 04 760 | 3/1988 |
| DE | 44 29 084 | 6/1995 |
| DE | 690 28 200 | 2/1997 |
| DE | 691 22 002 | 2/1997 |
| DE | 196 03 889 | 8/1997 |
| DE | 695 25 083 | 8/2002 |
| DE | 20 2006 000 329 | 3/2006 |
| DE | 20 2006 011 054 | 9/2006 |
| DE | 696 34 391 | 12/2006 |
| DE | 20 2007 003 398 | 6/2007 |
| DE | 10 2006 001 344 | 7/2007 |
| DE | 696 36 965 | 12/2007 |
| EP | 0 567 965 | 11/1993 |
| EP | 0 697 198 | 2/1996 |
| EP | 1 198 204 | 4/2002 |
| WO | 96/32891 | 10/1996 |
| WO | 98/18389 | 5/1998 |
| WO | 99/27859 | 6/1999 |

OTHER PUBLICATIONS

Brochure of Aesculap AG & Co. KG "Challenger Ti", 12 pages, Feb. 2002.

CARTRIDGE WITH A PLURALITY OF C-SHAPED LIGATURE CLIPS

This application is a continuation of international application number PCT/EP2010/054824 filed on Apr. 13, 2010 and claims the benefit of German application number 10 2009 018 820.7 filed on Apr. 24, 2009.

The present disclosure relates to the subject matter disclosed in international application number PCT/EP2010/054824 of Apr. 13, 2010 and German application number 10 2009 018 820.7 of Apr. 24, 2009, which are incorporated herein by reference in their entirety and for all purposes.

BACKGROUND OF THE INVENTION

The invention relates to a cartridge with a plurality of C-shaped ligature clips, with a housing accommodating ligature clips arranged in a row one behind the other and parallel to one another, with a transport element, which can be slid forward and back relative to the housing in the direction of the row and which when sliding forward and back relative to the housing causes at least one ligature clip to advance towards a discharge end of the cartridge.

Cartridges of this type are used in instruments, with which ligature clips can be placed against a vessel of the body in order to thus ligate the vessel. Such ligature clips are known in a wide variety of types and substantially consist of a C-shaped body with a bridge section and two legs that can be bent towards one another so that they constrict and clamp a section of a vessel between them.

In the case of known instruments of this type the ligature clips are arranged in a row one behind the other so that the legs run substantially parallel to the direction of advance of the ligature clips in the cartridge and point towards the discharge end of the cartridge with their free ends. The C-shaped ligature clips are advanced stepwise in the cartridge in the direction of the discharge end by a transport element. The respective ligature clip furthest forward is then slid in between two tools configured as clamping jaws, which compress the ligature clip after placement on the vessel section to be closed and thus secure it permanently on the vessel section. It is known in this case to alternately slide the transport element forward and back relative to the housing, wherein on each such step comprising sliding forward and back the ligature clips are respectively advanced by one position in the cartridge in the direction of the discharge end (DE 44 29 084 C1; EP 1 198 204 B1; DE 196 03 889 C2).

In known cartridges of this type the transport element is arranged in one plane next to the plane in which the ligature clips are located, so that the transport elements must be relatively stable in configuration to be able to absorb the bending moments that thus occur. Moreover, space is required beside the ligature clips, in which the transport element can be accommodated. In known cartridges both the transport element and the ligature clips must have their own guide means in the housing that assure precise relative movement and prevent a jam from occurring or prevent the transport elements from being deformed.

Cartridges are also known, in which the ligature clips located one behind the other are supported against one another so that all the ligature clips are advanced together in the cartridge by a feed element that acts on the ligature clip furthest to the rear. However, this requires that the consecutive ligature clips are supported against one another and a disadvantage with these designs is that production tolerances of the ligature clips accumulate and that substantial feeding forces must be transmitted by means of the feed element and in particular the ligature clips lying at the back (DE 695 25 083 T2).

It is necessary especially for minimally invasive surgery to provide placement tools for ligature clips that have the smallest possible dimensions, e.g. an elongate barrel with the smallest possible diameter. It is thus extraordinarily difficult to arrange a cartridge for ligature clips inside the available space and, moreover, the at least one transport element necessary for advancing the ligature clips.

It is an object of the invention to configure a cartridge of the above type so that a reliable advancing function of the ligature clips in the cartridge can be assured with the lowest possible design expenditure and small structural size.

SUMMARY OF THE INVENTION

This object is achieved according to the invention with a cartridge of the above-described type in that the ligature clips each have two legs connected by means of a bridge section and are divided by a longitudinal slit into two adjacent sections, which are only connected to one another in the region of the free ends of the legs, and that the transport element passes through the ligature clips arranged in a row in the space between the two adjacent sections of the ligature clips.

Ligature clips of the described type are known per se (DE 10 2006 001 344 A1), and it is also known to slide a row of such ligature clips onto a strip-like support, which passes through the space between the ligature clips. In this known arrangement the ligature clips are simply pulled off this support by means of a placement tool, whereas a transport element, which advances the ligature clips, or a housing, in which the ligature clips are accommodated for this, is not known in this context.

Because of the arrangement of the transport element in the space between the adjacent sections of the ligature clips, this space is used for the transport element which is supported in this space so that it can be slid forward and back in relation to the housing surrounding the ligature clips. In this case, the transport element and the ligature clips guide one another, the ligature clips prevent the transport element from buckling, since the ligature clips abut against the housing on the outside, while conversely the ligature clips are protected from tilting by the transport element, which runs on the inside of the ligature clips and passes therethrough in the longitudinal direction. A substantial advantage is the space saving, since no further transport element has to be arranged next to the ligature clips. This is accommodated inside the ligature clips and does not require any additional space and, moreover, the transport element is located in the plane of the ligature clips and in the centre thereof, so that no lateral bending moments act on the transport element that could lead to a deformation.

A particularly favourable mutual guidance is provided when the transport element according to a preferred embodiment of the invention abuts against the inner surfaces of the adjacent sections of the ligature clips.

A particularly advantageous configuration is one in which it is provided that the transport element has the form of a flat strip.

It is additionally advantageous if the ligature clips are disposed in the housing to be displaceable in the direction of the row by a guide means.

In a first preferred embodiment it is provided that the guide members of the guide means are arranged on the housing and the ligature clips are in guiding contact with the guide members. Such a guide member can be a longitudinal groove.

In a first preferred embodiment it is provided that the guide members of the guide means are arranged on the housing and guide elements arranged on the transport element and passing through the space between adjacent sections of the ligature clips are in guiding contact with the guide members. Therefore, in this case the guidance of the ligature clips is assured substantially by the transport element, which passing directly through the ligature clips is guided in the guide members of the housing.

In this case it can be provided that the guide elements of the transport element are resilient, so that ligature clips can be slid past them, wherein the guide elements are elastically displaceable into the inside area between the legs of the ligature clips. As a result of this, there is no hindrance to ligature clips sliding past the guide elements in one direction when the transport element is withdrawn relative to the ligature clips.

It is advantageous in this case if the spacings of adjacent guide elements of the transport element are different from the spacing of adjacent ligature clips in the housing or from a multiple of this spacing. As a result of this, it is assured that not all guide elements are pivoted into the inside area of the ligature clips simultaneously during the advance of the ligature clips and thus lose their guidance quality, instead this occurs because of the different spacings with different relative positions between the transport element, on the one hand, and the ligature clips, on the other, so that when a ligature clip slides past a brief loss of guidance always only occurs at some locations, while it is maintained at other locations.

Because of the fact that the ligature clips are guided by the transport element, on the one hand, and directly or indirectly by the housing, on the other, and that the transport element is also guided inside the ligature clips over its entire length, it can be provided that the ligature clips are guided loosely relative to the transport element and/or relative to the housing, but nevertheless are given adequate guidance and their orientation is maintained within the cartridge. It is thus possible to avoid a very close abutment of the ligature clips against the guide elements and high friction forces caused by this, but nevertheless a satisfactory guidance of the ligature clips results along the entire feed path.

It is particularly advantageous if according to a preferred embodiment it is provided that holding projections elastically deformable between an abutment position and a release position are arranged on the housing and on the transport element, and in the abutment position said holding projections abut against the ligature clips and prevent a displacement of the ligature clips against the direction of advance and are deformed by the ligature clips during their advance into the release position, in which the ligature clip can be moved past them in the direction of advance. As a result, the individual ligature clips are displaced by the holding projections with the relative position of the transport element and the housing, the transport element thus acts on the individual ligature clips and the ligature clips are not only simply advanced by a displacement force that only acts on the ligature clip furthest to the rear.

It is advantageous in this case if the number and spacings of the holding projections, possibly with the exception of the ligature clip furthest forward, are equal to the number and spacings of the ligature clips of the filled cartridge. In this case, such a holding projection, which displaces the ligature clip during the relative displacement of the transport element in relation to the housing, always acts on each ligature clip in the cartridge. It is possible that this is not the case with the ligature clip furthest forward, namely a special feeding means can be provided for advancing the ligature clip furthest forward.

However, in a modified embodiment it can also be provided that the spacings of adjacent holding projections along the row are different. This has the advantage that when the ligature clips slide past the holding projections not all holding projections are elastically deformed simultaneously, but at different times. As a result, there are always holding projections that are not elastically deformed by the ligature clips and that in the non-deformed state can assist in guiding the ligature clips in the cartridge.

In another configuration it is provided that only one respective projection is provided on the housing and the transport element for each group of a plurality of ligature clips arranged in a row one behind the other. For example, it could be provided that the holding projections have double the spacing of the ligature clips in the cartridge, so that only one holding projection is provided for every second ligature clip. During displacement of a ligature clip in this case, this entrains the ligature clip arranged in front of it forwards, then only the next ligature clip but one is advanced again by a holding projection of the transport element and housing. The friction forces can be reduced as a result of this, since in particular when the holding projections are withdrawn and slid past the ligature clips there are fewer positions present, at which a holding projection slides over a ligature clip in elastically deformed state.

The holding projections, which prevent the ligature clips from sliding back, can be arranged on the housing. However, in a modified configuration it can be provided that a retaining element, which is connected to the housing, is non-displaceable relative to the housing in the direction of the row and which has elastically deformable holding projections, is arranged adjacent to the transport element in the space between the adjacent sections of the ligature clips. Therefore, in this case the holding projections are not arranged on the housing, but on a retaining element, which is connected to the housing such that this retaining element is non-displaceable relative to the housing in the direction of the row. The transport element and the retaining element can be configured as flat strips abutting flat against one another.

It is advantageous in this case if the transport element has a longitudinal groove, in which the retaining element is received in a guided manner.

In an arrangement, in which for a group of a plurality of ligature clips arranged in a row one behind the other only one holding projection is respectively provided on the housing or the retaining element, on the one hand, and the transport element, on the other, difficulties may result for the ligature clips furthest to the rear under some circumstances if these are not provided with their own holding projection, i.e. if these are positioned between two holding projections. In order to also assure a satisfactory feed in this case, it can be provided that a feed member follows the last ligature clip of the row and is displaced in the direction of advance in the same manner as the ligature clips. This replaces, as it were, the ligature clips missing after the last ligature clip and is advanced in the same way as the ligature clips themselves, so that this feed member also advances the last ligature clip arranged in front of it if this is not positioned next to a holding projection. Therefore, in other words, it is provided that the feed member advances the last ligature clip and, if necessary, ligature clips arranged in front of this and in contact with the respective following ligature clip in the direction of the discharge end of the cartridge. Such a group formation is naturally not restricted to the case that a holding projection is provided for every second ligature clip. More ligature clips, e.g. three or four, can also be combined in the group, so that the spacing of the holding projections then accordingly amounts to three-times or four-times the spacing of the ligature clips in the cartridge.

According to a first preferred embodiment, the feed member can be resiliently-biased in the direction of advance, so that the respective last ligature clips are advanced thereby, but it is also possible that the feed member is advanced by the relative displacement of the transport element and the housing in the same way as the ligature clips. For this, the feed member practically replaces the ligature clips missing behind the last ligature clip and has similar abutment surfaces to the ligature clip, against which the holding projections can abut.

In particular, it can be provided that the feed member has an inner space, into which the transport element enters in a guided manner when the feed member advances, so that the feed member guides the transport element in the region in which the transport element had previously been guided by ligature clips. Therefore, the feed member assumes the guidance role of the ligature clips as soon as the ligature clips are partially removed from the cartridge and are partially advanced in the cartridge in the direction of the discharge end.

In a particularly preferred embodiment it is provided that holding projections are arranged on the transport element only for the ligature clip furthest forward adjacent to the discharge end of the cartridge. Therefore, whereas in the above-described configurations of the transport element this advances all the ligature clips—possibly with the exception of the one furthest forward—in the cartridge, in this configuration a transport element is used that exclusively displaces the ligature clip furthest forward, whereas the rest of the ligature clips are advanced in a different manner in the cartridge.

A particularly favourable configuration is one in which it is provided that a first transport element and a second transport element are arranged in the space between the adjacent sections of the ligature clips so that they can be slid forward and back relative to the housing, the second transport element of which effecting the advance of the ligature clip furthest forward and the first transport element effecting the stepwise advance of all following ligature clips. Therefore, in this configuration two adjacent transport elements in the space between the ligature clips are used that have different functions and are nevertheless guided jointly in the space between the ligature clips and conversely also guide these.

It can also be provided here that the first and the second transport element are configured as flat strips abutting flat against one another.

It is particularly advantageous if one of the two flat strips has a longitudinal groove, in which the other flat strip is received in a guided manner.

For sliding the transport element forward and back, a slide can be disposed on the housing so that it can be slid forward and back in the direction of advance, said slide being connected to the transport element by means of intermeshing projections and recesses, so that the slide entrains the transport element at least during a portion of its sliding movement.

In this case, it is particularly advantageous if in the case of a cartridge with a first transport element and a second transport element in the space between adjacent sections of the ligature clips the slide is in an entrainment connection with both transport elements, whereby the slide entrains the first transport element and the second transport element over different portions of its own sliding movement. Therefore, while the slide executes a uniform movement forward and back, it transmits this to the two transport element by the entrainment means in a different manner. For example, it can be provided that the first transport element, which effects the stepwise advance of all ligature clips with the exception of that furthest forward, is only entrained over a portion of the sliding movement of the slide, whereas the second transport element, which displaces the ligature clip furthest forward to the discharge end of the cartridge and possibly beyond that, is entrained over the entire sliding movement of the slide. Thus, an advancing movement is possible for the ligature clip furthest forward that covers a larger path than the advancing movement for the rest of the ligature clips, and therefore the clip furthest forward can be advanced out of the cartridge into a clamping means, the distance of which from the cartridge can be greater than the spacing between consecutive ligature clips in the cartridge.

For example, it is favourable if the slide engages by means of a projection into a recess of the first transport element, which in displacement direction is longer than the projection and shorter than the sliding movement of the slide. Thus, an entrainment of this transport element will only occur during a portion of the sliding movement of the slide.

However, it is also possible that the slide engages by means of a projection into a recess of the second transport element, which in displacement direction is equal in length to the projection. Thus, the displacement movement of the slide is transmitted to its full extent to the second transport element.

In a preferred embodiment it is provided that the entrainment connection between slide and transport element is arranged along the transport element so that during the forward and/or return movement the transport element is under tension at least in a portion of its longitudinal extent and not under compression.

For example, it can be provided that a first entrainment connection for the advance in the direction of the discharge end of the cartridge and a second entrainment connection for the opposed return movement are provided between the slide and transport element, and the first entrainment connection lies closer to the discharge end than the second entrainment connection.

In this case, it is additionally advantageous if the entrainment connection adjacent to the discharge end of the cartridge comprises an elastically deformable entrainment means, which can slide elastically past a ligature clip located behind the slide during the return movement thereof. The advancing movement of the ligature clip is not impaired by the entrainment means as a result of this.

According to a first configuration of the invention, the holding projections on the transport element or on the retaining element can be configured as pivoted out tongues, which are separated out of the plane of the transport element or the retaining element by a C-shaped dividing line and which can be pivoted elastically into the plane of the transport element or the retaining element. In the pivoted-out state these tongues are supported on the ligature clips and in the pivoted-in state the ligature clips can slide past them.

In another configuration it is provided that the holding projections on the transport element are arms lying in the plane of the transport element, which protrude upwards and/or downwards from a longitudinal edge and can be pivoted elastically in towards the opposite longitudinal edge of the transport element, and which arms in the pivoted-out state pass from the inside outwards through the space between the adjacent sections of the legs of the ligature clips and in the pivoted-out state abut against the connection of the adjacent sections of the ligature clip at the free end of the legs.

It is particularly favourable in this configuration if in the pivoted-out state the arms are guided outside the legs of the ligature clips in a longitudinal guide means of the housing.

The arms thus assume a double function, namely the guidance of the transport element and the ligature clips on the housing, on the one hand, and the advancing movement for the ligature clips, on the other.

In the configurations described so far, the holding projections on the transport elements or on the retaining elements are configured as elastically deformable tabs or holding lugs. However, in a modified embodiment it is possible that in place of elastically deformable holding projections on the transport elements and/or the retaining element non-deformable holding projections are provided, which lie in the plane of the transport element and/or the retaining element and protrude upwards and/or downwards from a longitudinal edge, and which on one side have a slide surface, on which the ligature clips can slide on approach with elastic expansion and thus can slide past the holding projection, whereas on the opposite side they have an abutment surface, which on approach abuts against the ligature clip and thus prevents the ligature clip from sliding past the holding projection.

In particular, such a holding projection can have the form of a saw tooth.

Therefore, in this configuration the ability of the legs of the ligature clip to bend up elastically is used, these legs being elastically bent up when they slide past a holding projection. However, sliding past such a holding projection is only possible respectively in one direction, while in the opposite direction the holding projection abuts against the ligature clip in such a way that this cannot be slid past the holding projection.

The guidance between the transport element and the ligature clips is of particular importance in the case of the ligature clip furthest forward. Namely, according to a preferred embodiment it can be provided that in the case of the ligature clip furthest forward in the row, the transport element projects into the space between the sections. This ensures that the ligature clip furthest forward is also still provided with guidance when leaving the cartridge and thereafter by the pushed forward transport element, in particular also when the feed path does not run exactly rectilinearly between the clamping jaws adjoining the cartridge, but instead has a curved course. A transport element configured as a flat strip can follow this curved course and thus also guide the ligature clip along this curved feed path.

In a preferred embodiment it is provided that clamping elements, which during discharge and/or after discharge from the cartridge secure the ligature clip furthest forward against displacement along the row, are arranged at the discharge end of the cartridge. This can be important when the transport element that slides the ligature clip furthest forward out of the cartridge and in between the adjoining clamping jaws is withdrawn. It is then ensured by the clamping jaws that the ligature clip furthest forward remains in its position and does not change its position in an undefined manner.

For example, the clamping elements can be formed by clamping jaws, which adjoin the cartridge in the direction of advance, between which the ligature clip furthest forward is inserted after discharging from the cartridge and the spacing of which is dimensioned so that the legs of the ligature clip are bent towards one another. The bending of the legs can be elastic or permanent, i.e. non-elastic, in this case. As a result of this bending the legs are clamped against the clamping jaws, and this clamping or frictionally engaged arrangement holds the ligature clip furthest forward in the position reached.

In another embodiment it can be provided that the clamping elements are holding members, which are arranged on the cartridge, penetrate into the feed path of the ligature clip furthest forward, abut against the ligature clip furthest forward when sliding past it and are thus elastically removable by it out of the feed path. These holding members are clamped against the ligature clip furthest forward when this is advanced and thus pushes the clamping elements elastically out of the feed path.

The following description of preferred embodiments of the invention serves for more detailed explanation in association with the drawing.

DETAILED DESCRIPTION OF THE INVENTION

Figure 1:
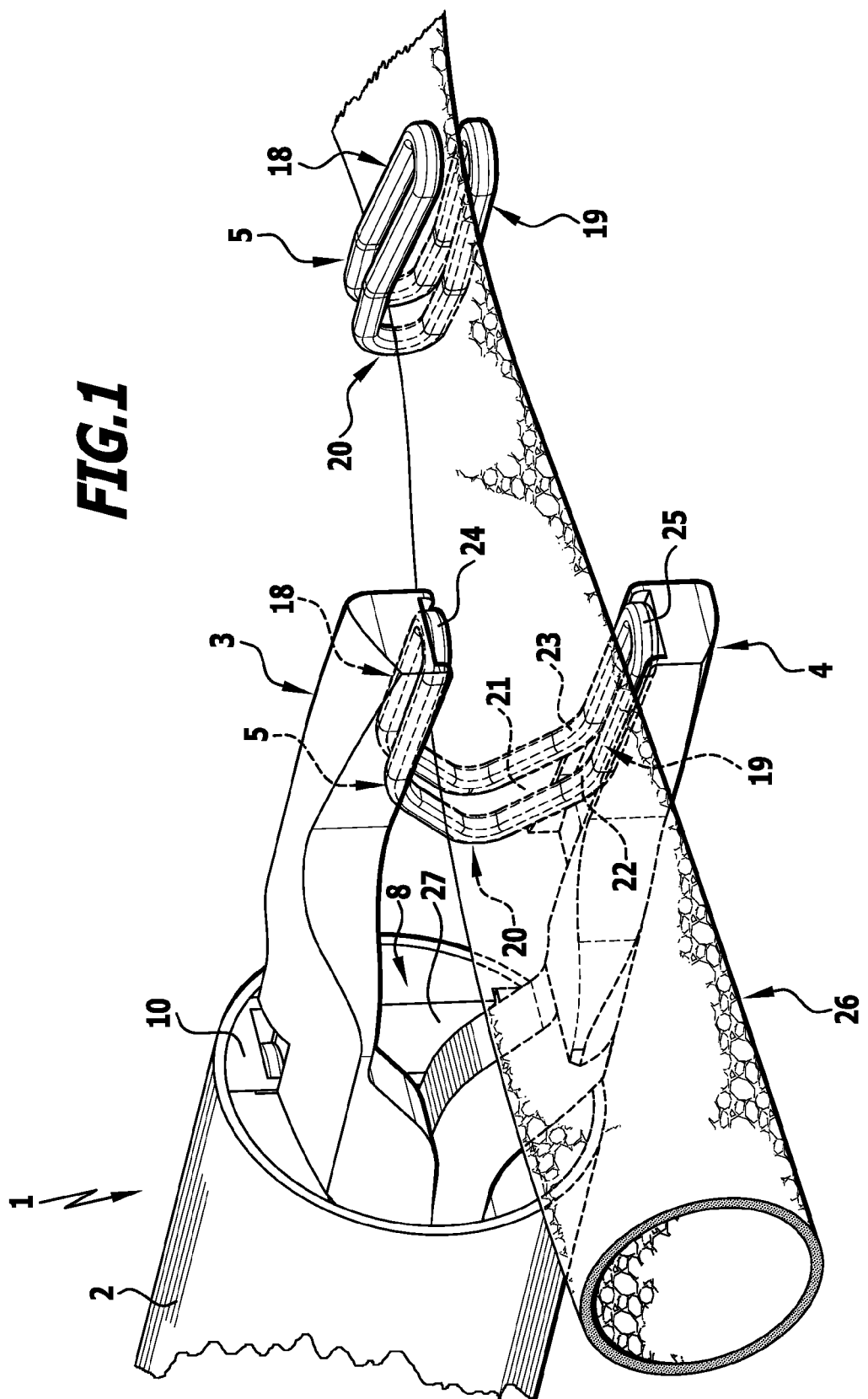
FIG. 1 is a perspective view of a surgical placement instrument for ligature clips in the region of the clamping jaws with a ligature clip in place and a ligature clip placed against a vessel and not yet closed.
Figure 2:
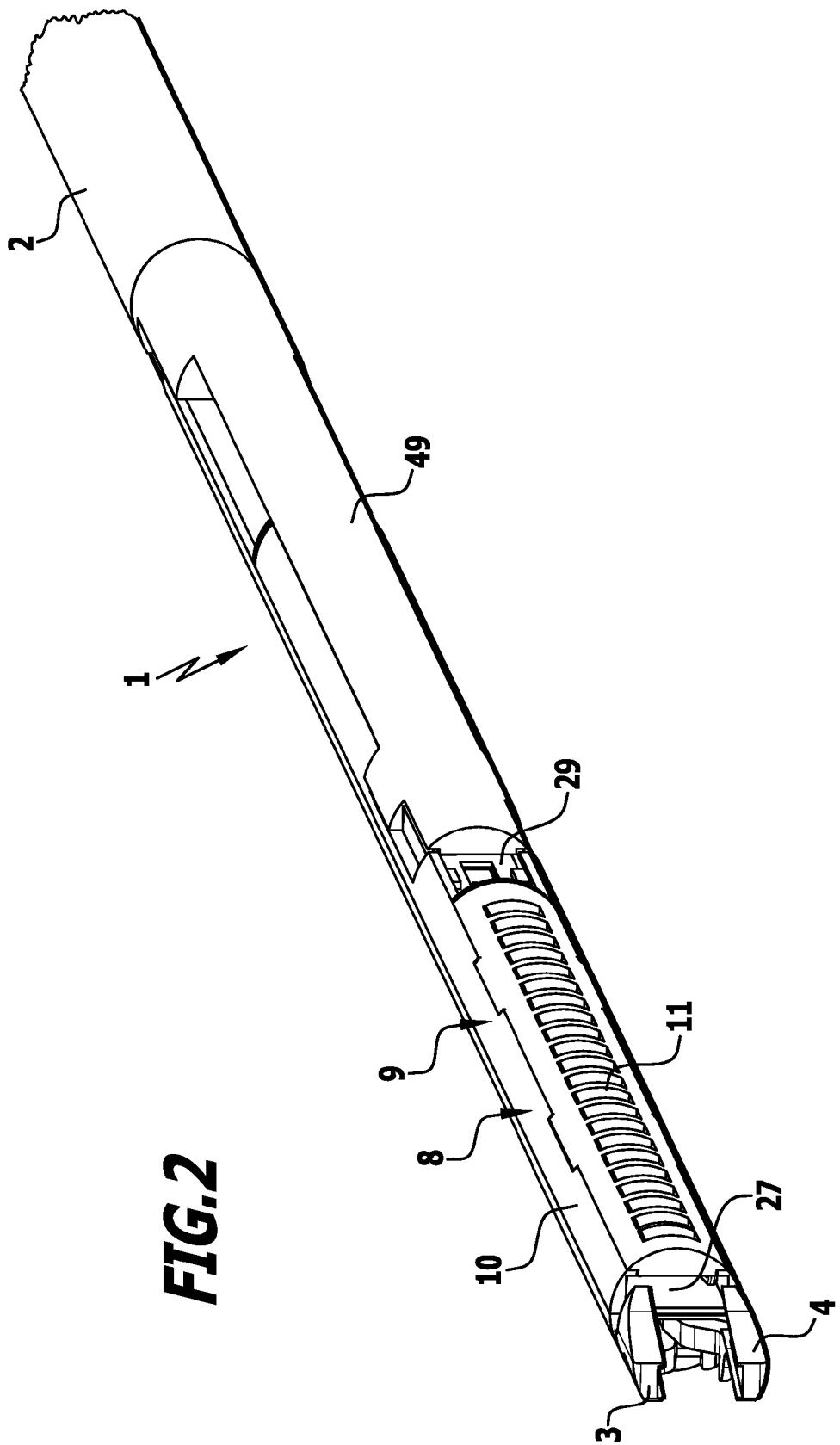
FIG. 2 is a perspective view of the front portion of the placement instrument of FIG. 1 with a cartridge for ligature clips inserted into the instrument.
Figure 3:
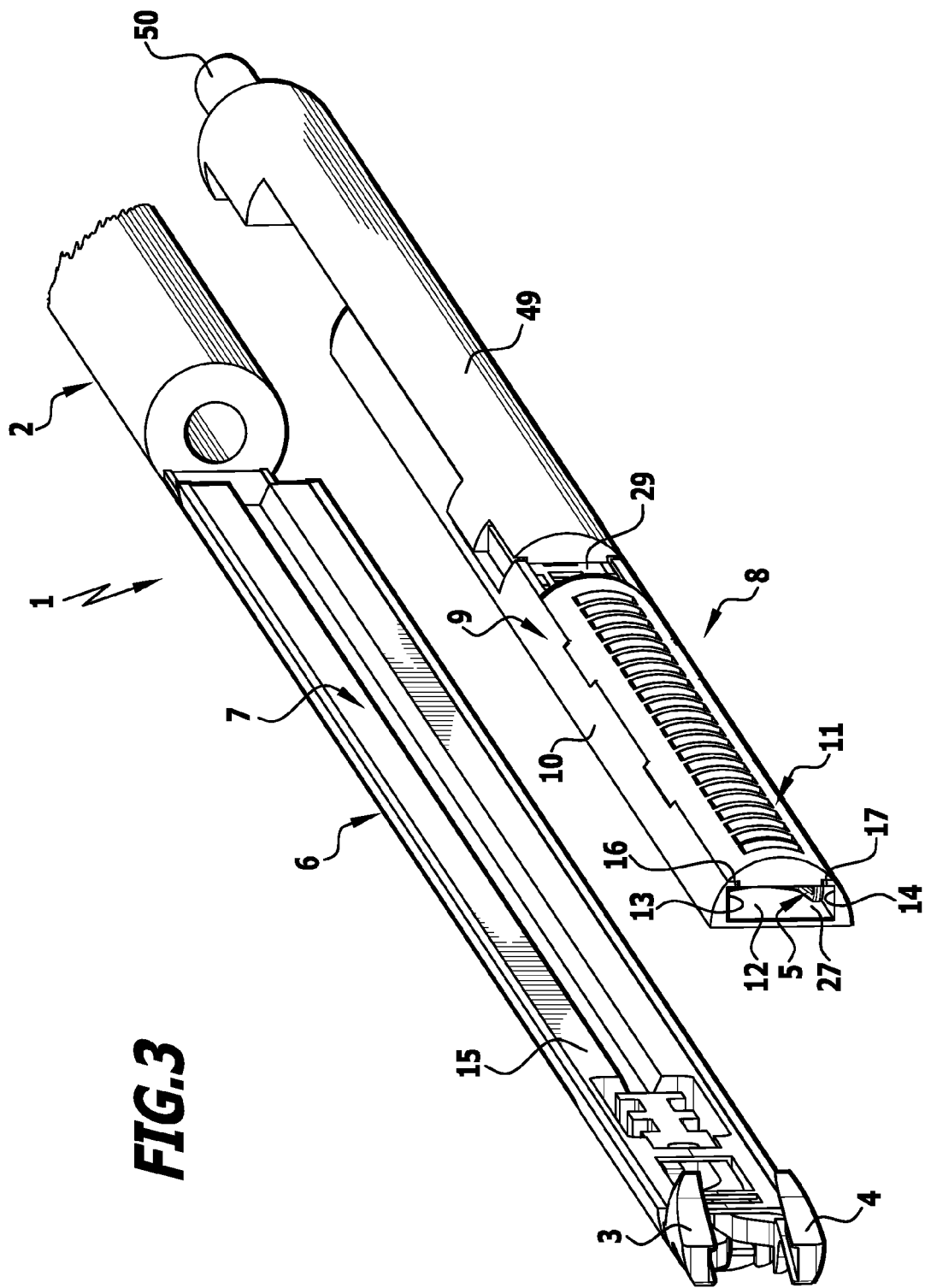
FIG. 3 is a view similar to FIG. 2 with the cartridge before insertion into the placement instrument.

The placement instrument 1 shown in the drawing comprises an elongated tubular barrel 2 bearing two clamping jaws 3, 4 at its distal end, which are movable relative to one another transversely to the longitudinal direction of the barrel 2, so that a ligature clip 5 inserted between the clamping jaws 3, 4 can thus be deformed from an open position into a closed position. The drive of the clamping jaws 3, 4 is a conventional drive, which is not specially shown in the drawing, and this drive is activated by a transmission member, which passes through the barrel 2 in the longitudinal direction and can be moved by an actuating element, e.g. a pivoting lever, at the proximal end of the barrel 2 in a handle.

The tubular barrel can have a circular cross-section, but the cross-section of the barrel 2 is reduced in a section 6 directly adjoining the clamping jaws 3, 4, e.g. the barrel 2 still has the cross-section of a semicircle or the cross-section of a sector there, so that next to this section 6 with a reduced cross-section a receiving space 7, into which a cartridge 8 can be inserted, is configured in the circular cross-section of the rest of the barrel 2. This cartridge 8 serves to accommodate a substantial number of ligature clips 5, which can be advanced individually one after the other out of the cartridge 8 between the clamping jaws 3, 4 by means explained in detail below, so that the clamping jaws 3, 4 are supplied with a respective ligature clip for the consecutive placement of ligature clips.

The cartridge 8 has a housing 9 with a guide part 10 with a C-shaped cross-section and a cover 11, which can be attached to this guide part 10 and is detachably connected to the guide part 10. The guide part 10 has a plane base 12 and two side walls 13, 14 projecting perpendicularly therefrom and arranged parallel to one another, the inner space thus being an inner space with a rectangular cross-section, which runs along the entire length of the guide part 10 in the manner of a longitudinal groove and is open at least at its distal end directed towards the clamping jaws 3, 4. In the inserted state, the guide part 10 abuts with the base 12 flat against a plane abutment surface 15 of the barrel 2, which extends along the entire receiving space 7, and there the cartridge 8 is detachably connected to the barrel 2 in this position, e.g. by an elastic locking connection, which is not shown in more detail in the drawing. The outer cross-section of the housing 9 is shaped such that it is adapted to the circular cross-section of the barrel 2, so that the cartridge 8 fills the receiving space 7 and together with the semicircular or sector-shaped portion of the barrel 2 in the region of the receiving space 7 generates a circular cross-section that preferably has the same diameter as the adjoining portion of the barrel 2.

The side walls 13, 14 bear inwardly projecting guide bars 16, 17 running along their free edges, so that the side walls form a guide path with the base 12, on the one hand, and these guide bars 16, 17 on the other, against which ligature clips 5 stored in the cartridge 8 abut in a guided manner.

In the open state the ligature clips 5 stored in the cartridge 8 have a substantially C-shaped cross-section with two legs 18, 19 running parallel to one another and connected to one another at one end by means of a bridge section 20. In the open state the legs 18, 19 have a spacing from one another that is large enough to receive a vessel, on which the ligature clip 5 is to be placed. A longitudinal slit 21 dividing the ligature clip into two adjacent sections 22, 23 runs over the entire length of the legs 18, 19 and the bridge section 20, and these adjacent sections 22, 23 are only connected to one another in the region of the free ends of the legs 18, 19, the connection in this region being circular arc-shaped in the shown exemplary embodiment. Therefore, as a result of the longitudinal slit 21 a space extending substantially over the entire length of the ligature clip is configured between the adjacent sections 22, 23 and terminates at the connections 24, 25 in the region of the free end of the legs 18, 19 (FIG. 1).

To close the ligature clip, this is deformed by the clamping jaws 3, 4 as they approach so that the two legs 18, 19 are moved relative to one another while remaining substantially parallel to one another, and the ligature clip is thus deformed in the region of the bridge section 20 and the legs 18, 19 are clamped against the vessel 26 and remain in this closed position.

The ligature clips are preferably made of metal, in particular titanium or a titanium alloy.

Figure 4:
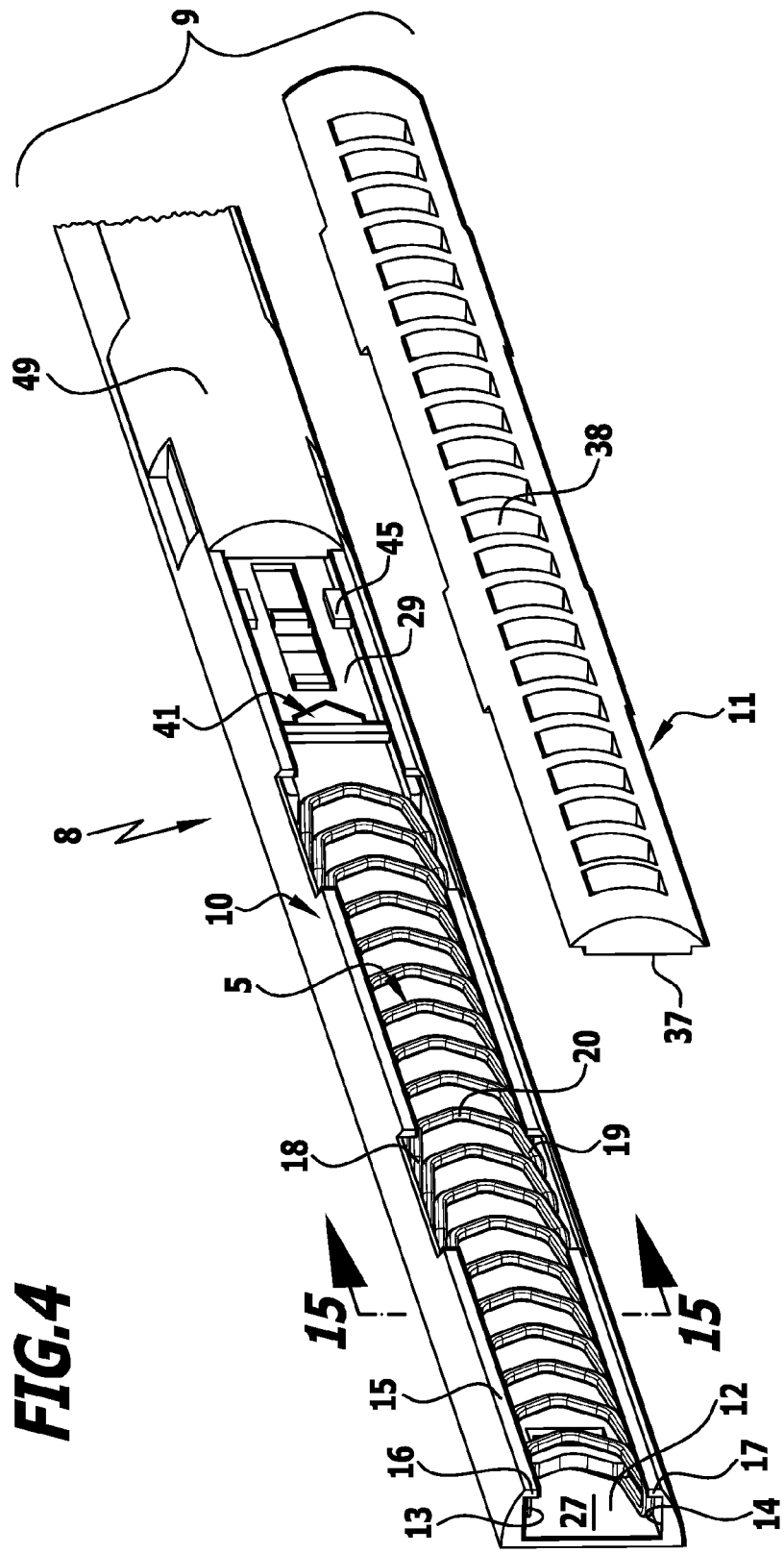
FIG. 4 is a perspective partial view of the cartridge with the cover removed.
Figure 5:
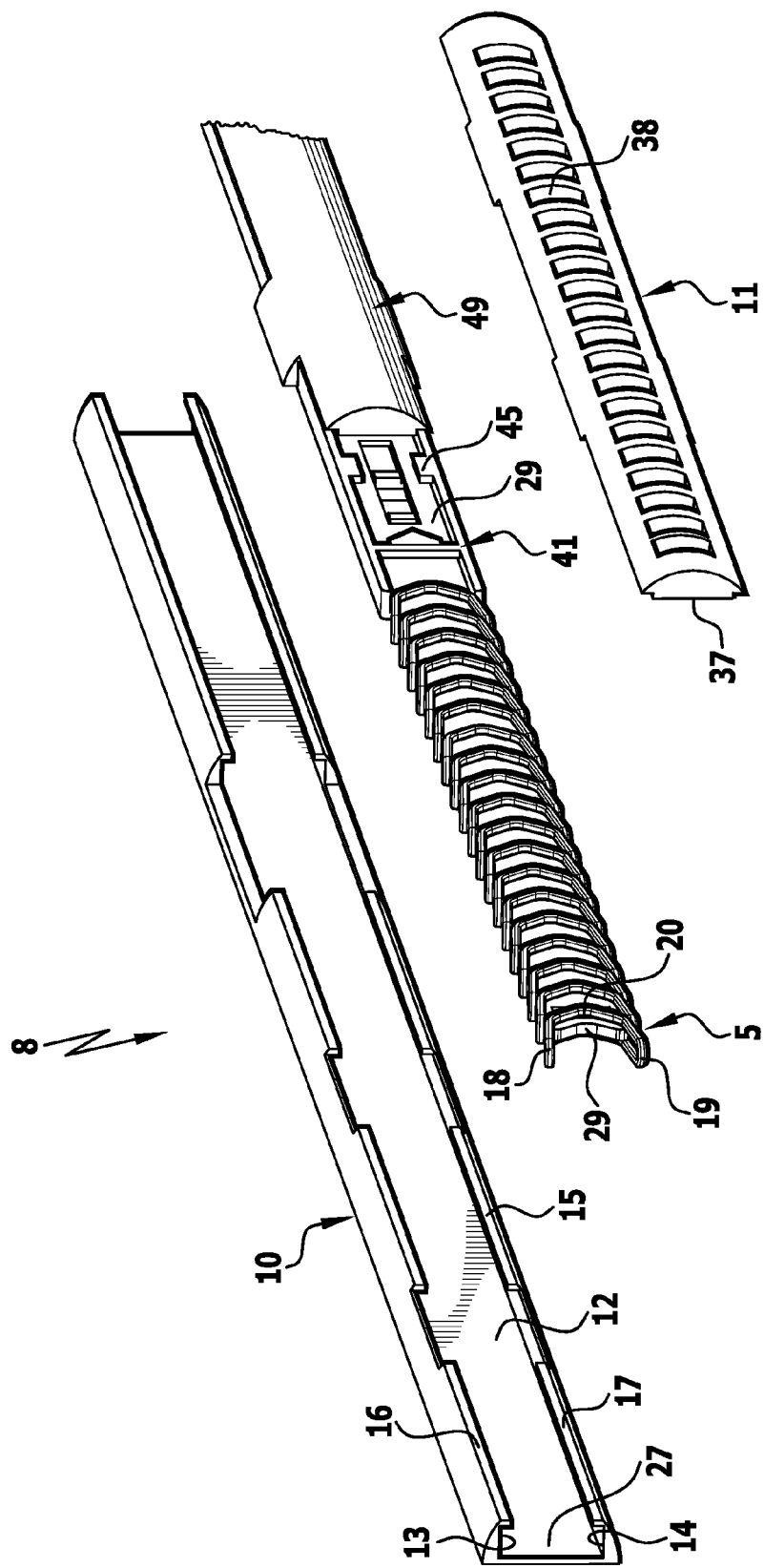
FIG. 5 is a perspective view similar to FIG. 4 with an additionally removed rear housing part.
Figure 6:
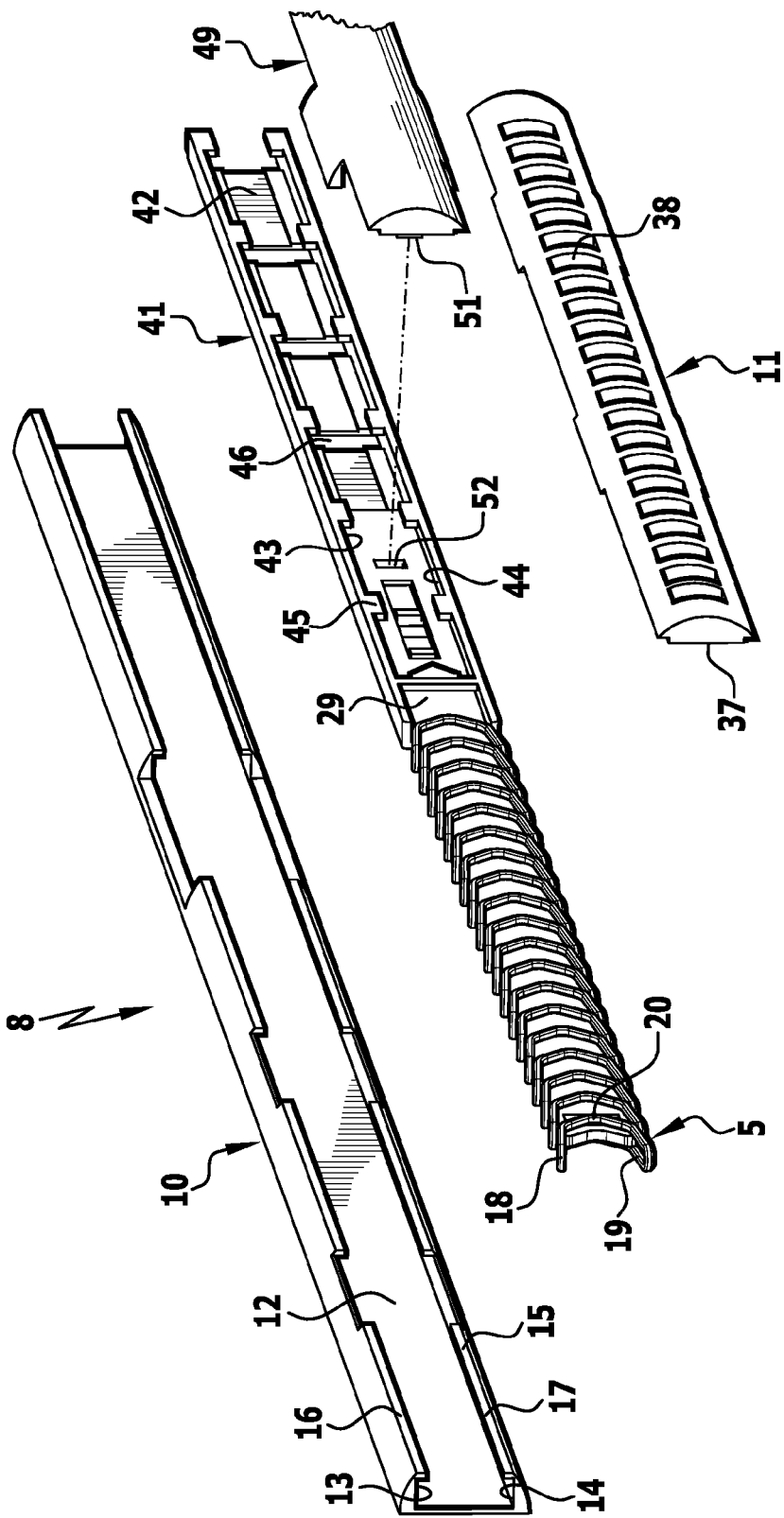
FIG. 6 is a view similar to FIG. 5 with an additionally removed slide for operation of the cartridge.
Figure 7:
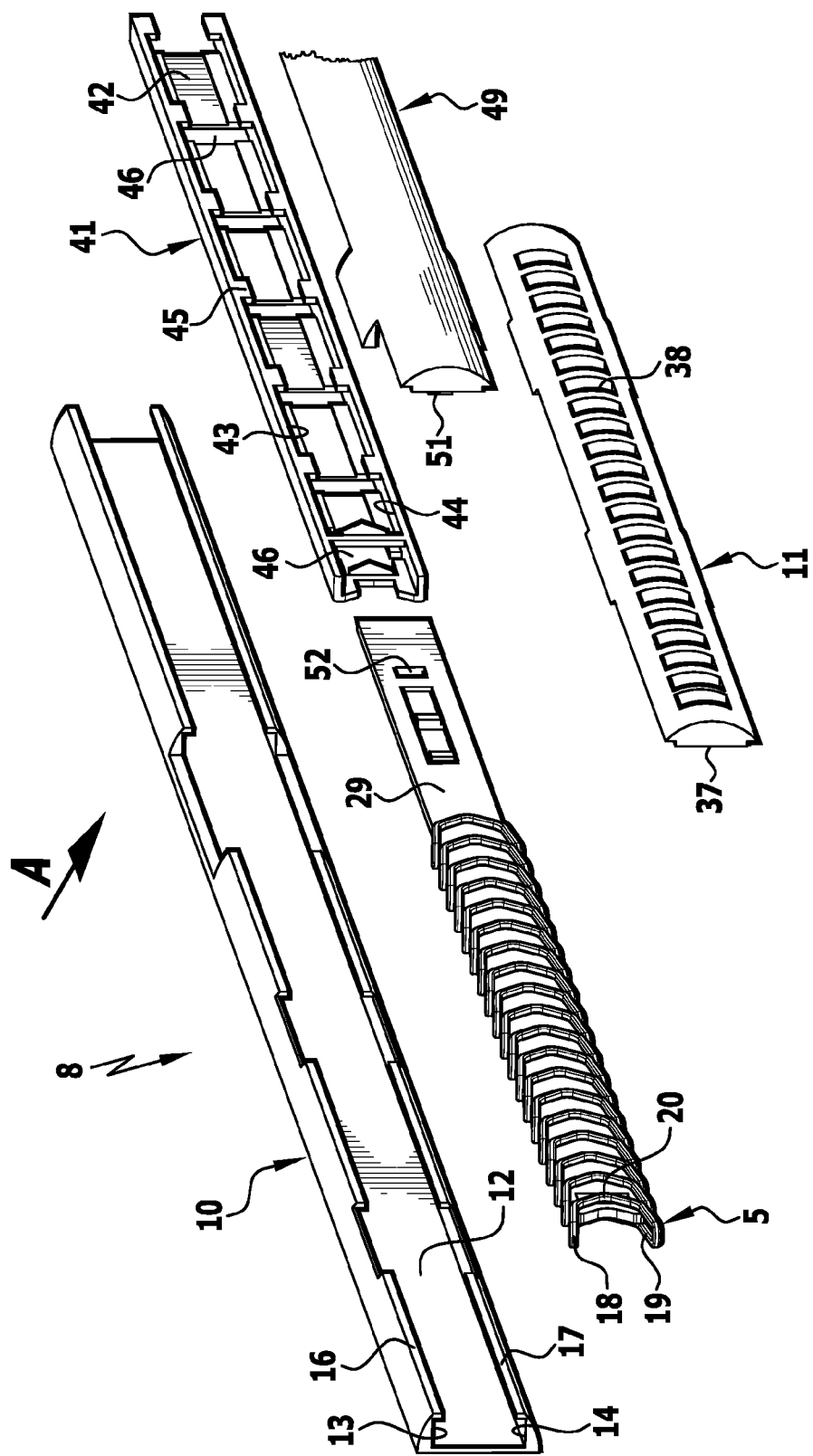
FIG. 7 is a view similar to FIG. 6 with feed member pulled off to the rear in the longitudinal direction of transport elements passing through the ligature clips.
Figure 8:
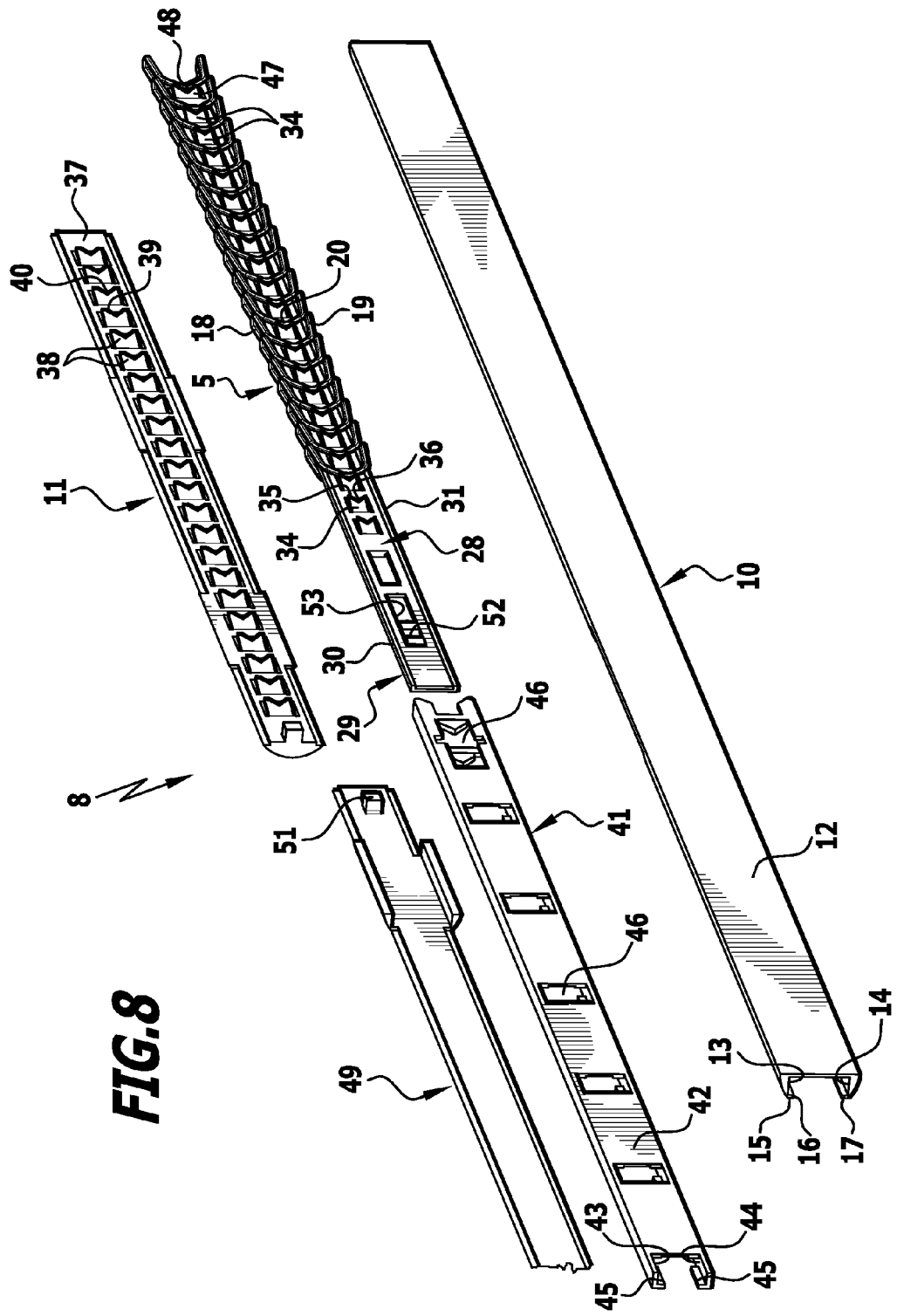
FIG. 8 is a perspective view corresponding to FIG. 7 in the direction of arrow A in FIG. 7.
Figure 9:
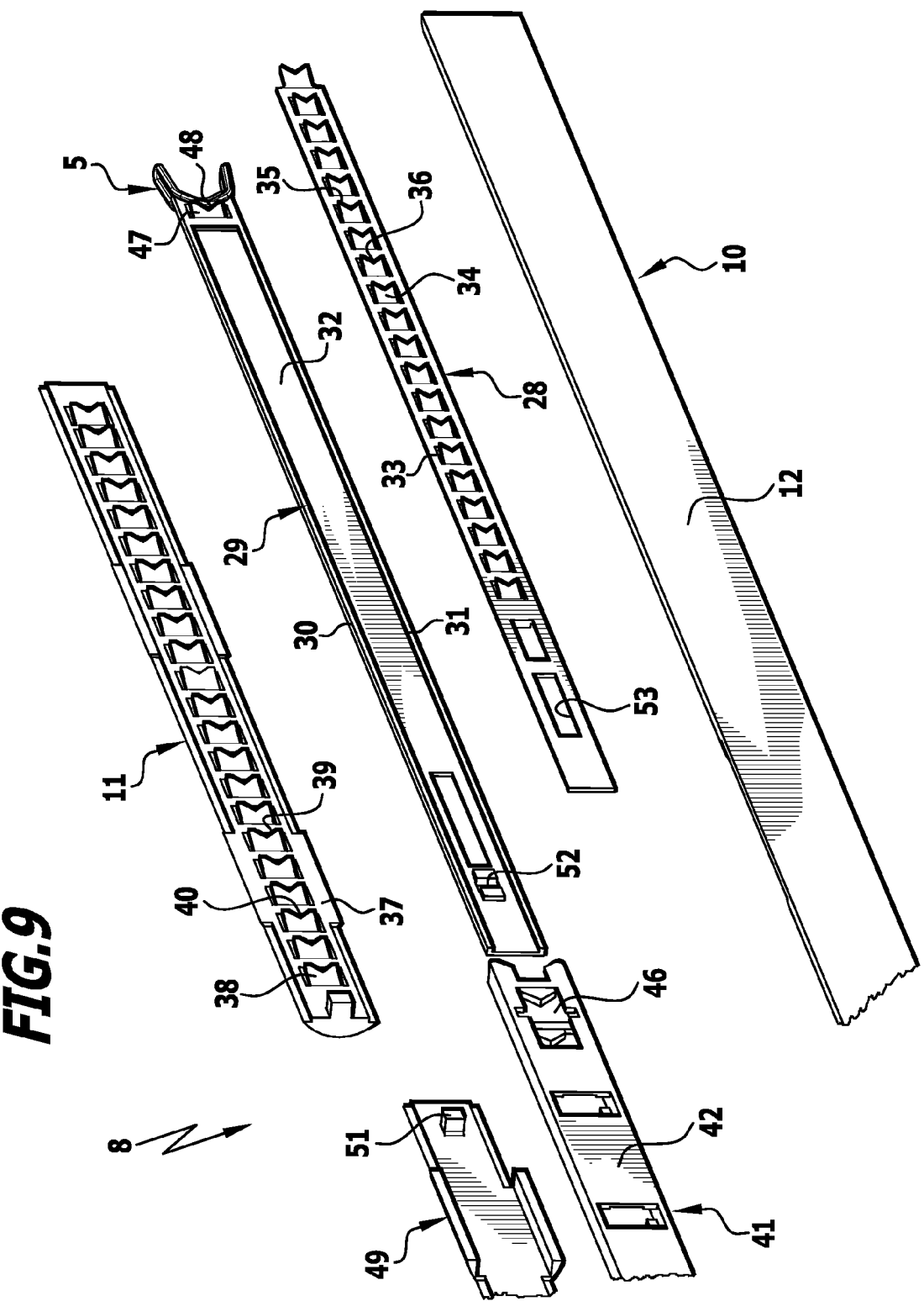
FIG. 9 is a view similar to FIG. 8 with a first transport element without ligature clips and a separately illustrated second transport element for the ligature clip furthest forward.

A multiplicity of such ligature clips 5 are laid one behind the other in the guide part 10 of the cartridge 8 so that the outer surfaces of their legs 18, 19 abut against the side walls 13 and 14 respectively with the free ends of the legs 18, 19 thus pointing in the direction of a discharge end 27 of the cartridge, which directly adjoins the clamping jaws 3, 4. In this case the width of the ligature clips 5 corresponds to the spacing of the guide bars 16, 17 from the base 12, so that the legs 18, 19 are displaceably guided in the guide part 10 through the guide groove formed by the side walls, the base and the guide bars in the longitudinal direction of the guide part 10. The ligature clips 5 laterally abut against the base 12, which thus additionally contributes to the guidance of the ligature clips 5 (FIG. 4). The legs of the ligature clips 5 can run parallel to the side walls 13, 14, but it is also possible that the legs 18, 19 do not run exactly parallel to one another, but are pivoted outwards, and then the legs 18, 19 only engage into the guide groove formed by the base 12, the side walls 13, 14 and the guide bars 16, 17 with their free ends, but this is sufficient for good guidance.

Two transport elements 28, 29 formed from a flat strip material and abutting flat against one another are passed through the spaces between the ligature clips 5 formed by the longitudinal slits 21, and these transport elements together fill the spaces substantially completely and thus additionally guide the ligature clips 5. The transport elements 28, 29 are disposed in the spaces to be freely displaceable relative to the ligature clips in the longitudinal direction. A first transport element 28 is slightly narrower than the second transport element 29, and this second transport element 29 bears a respective guide bar 30 and 31 projecting laterally to one side along the upper edge and along the lower edge, so that a receiving space 32 in the form of a longitudinal groove results, into which the first transport element 28 is inserted. The first transport element 28 is thus guided and disposed to be displaceable in the longitudinal direction relative to the second transport element 29, and in this case the guide bars 30, 31 project from the second transport element 29 so far that they are flush with the first transport element 28 inserted into the receiving space 32. In this case, the total thickness of the two transport elements 28, 29 abutting flat against one another is slightly less than the width of the longitudinal slit 21 in the ligature clips 5, so that good guidance of the ligature clips is provided by the transport elements 28, 29, but no frictional engagement and no clamping occurs.

Figure 15:
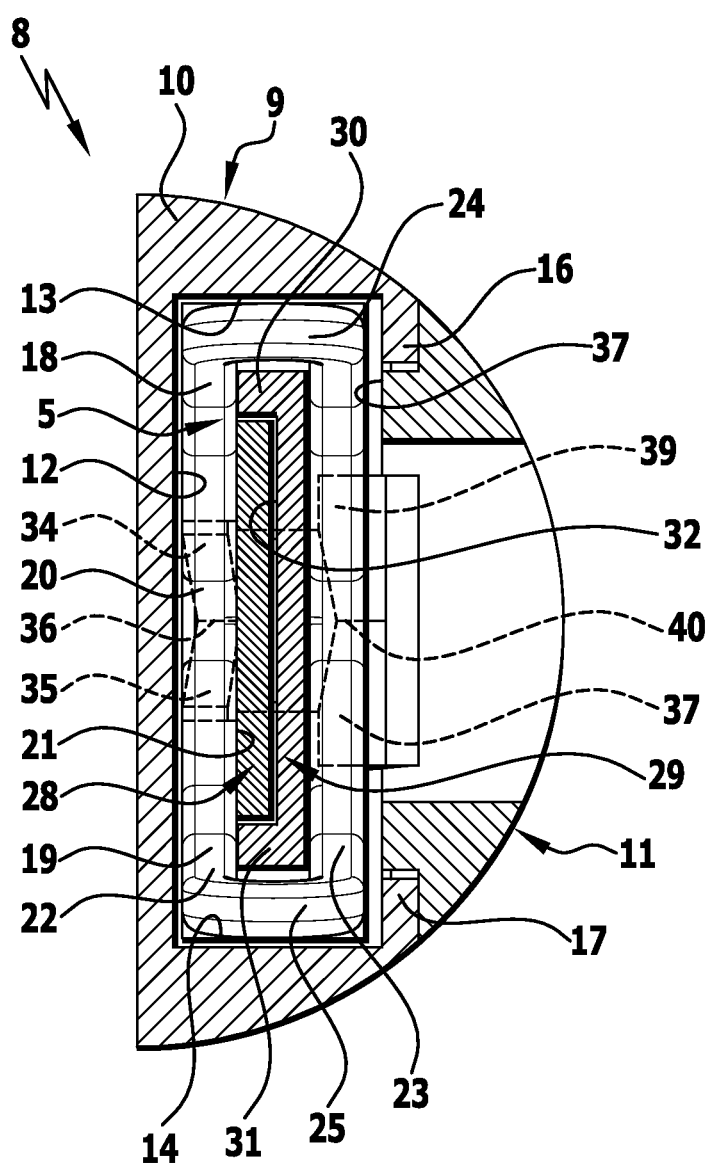
FIG. 15 is a sectional view taken along line 15-15 in FIG. 4.

The thickness of the transport elements 28, 29 lies between 0.1 mm and 2 mm, preferably between 0.4 and 1 mm, and therefore these are very thin structural parts, which are themselves guided by the ligature clips 5 and are protected from deformation, in particular from buckling, since the ligature clips are guided in the guide part 10 as well as by the cover 11, which is attached to this guide part 10 and abuts against the ligature clips 5 on the side thereof opposite the base 12 and laterally guides them there (FIG. 15).

Figure 10:
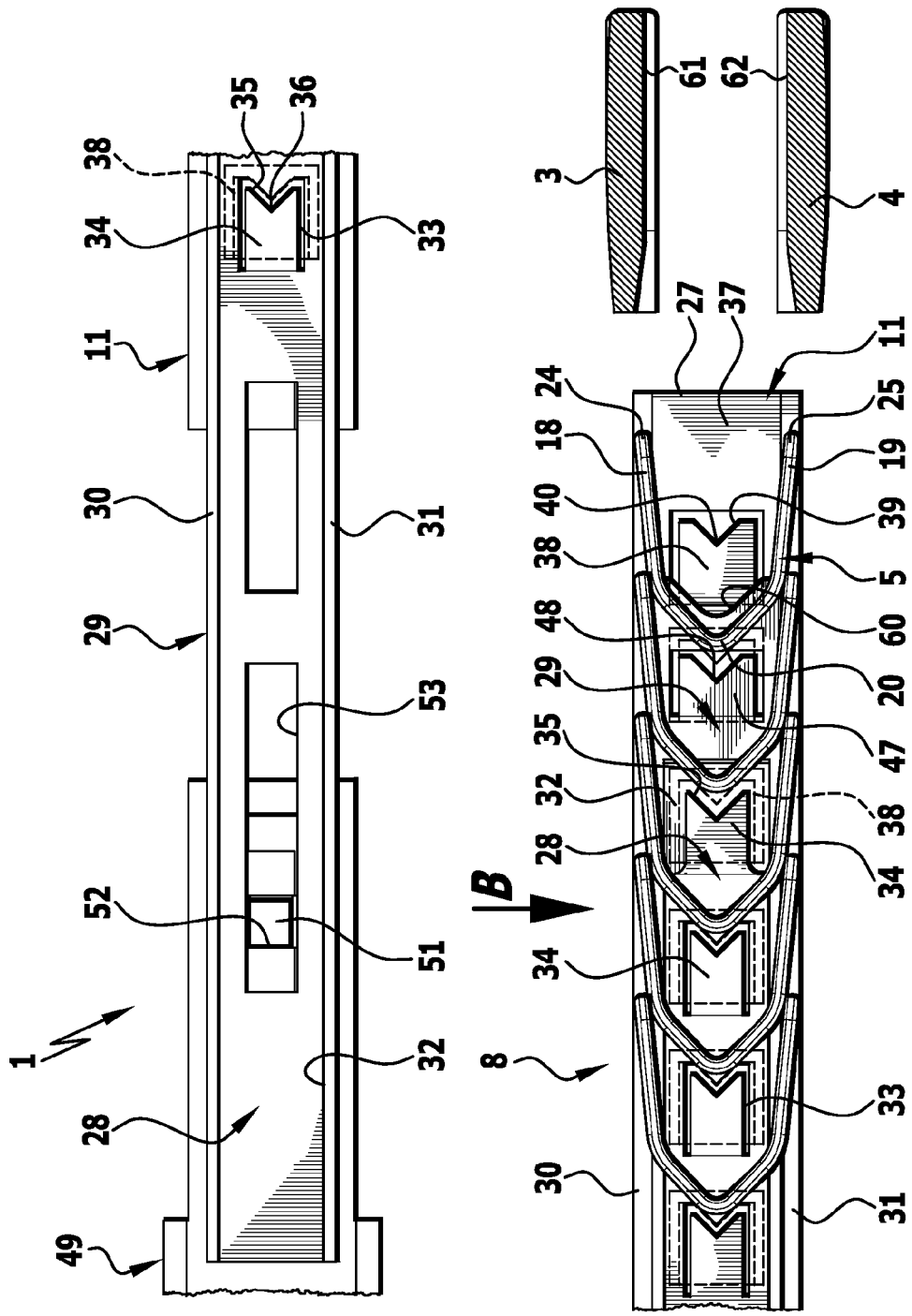
FIG. 10 is a side view of the two transport elements abutting against one another with ligature clips in the cartridge.
Figure 11:
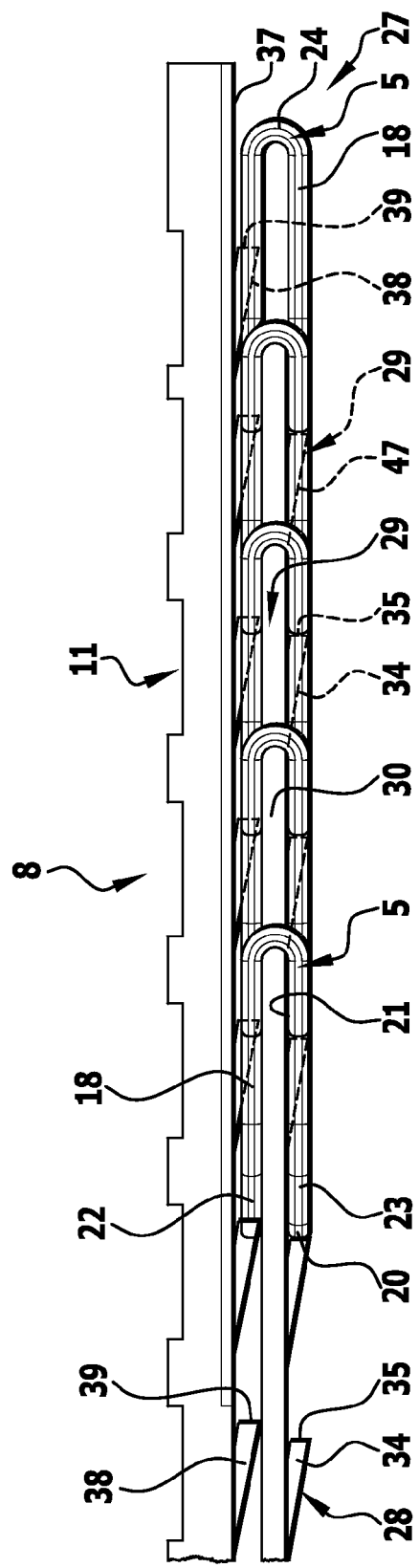
FIG. 11 is a view of the transport elements in the direction of arrow B in FIG. 10.
Figure 12:
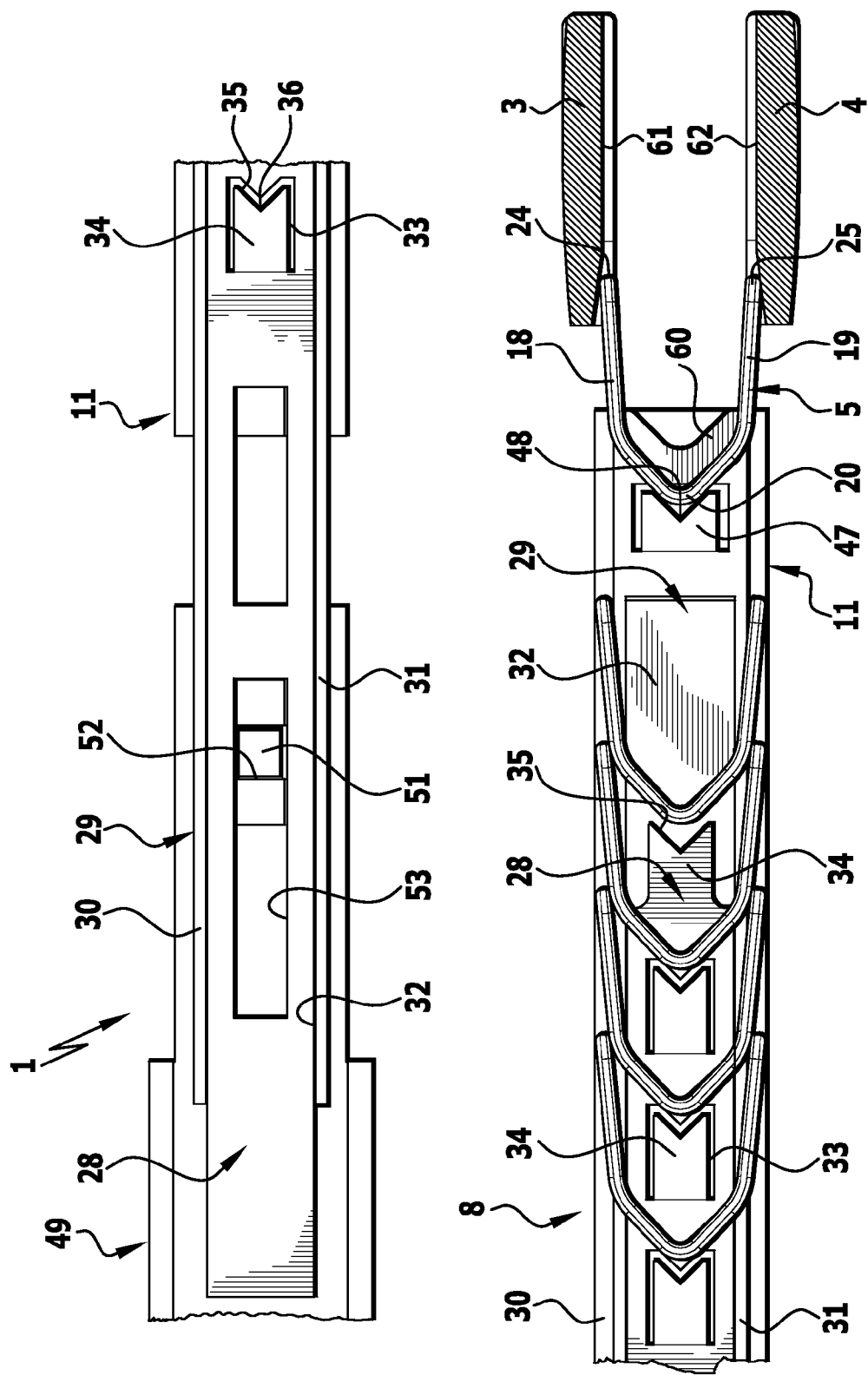
FIG. 12 is a view similar to FIG. 10 on insertion of the ligature clip furthest forward between two clamping jaws.

Over its length the first transport element 28 has a multiplicity of holding tongues 34, which are separated by a U- or C-shaped separation cut 33 and bent laterally out of the plane of the transport element 28 to point away from the second transport element 29, their front edge 35 pointing in distal direction. This front edge 35 can have a notch-shaped cutout 36, so that this front edge 35 can abut substantially along a line against the outer surface of the bridge section 20 of a ligature clip 5 (FIG. 10). The number of holding tongues 34 and their spacing from one another correspond to the number of ligature clips 5 and their spacing in the cartridge 8, so that each ligature clip 5 has such a holding tongue 34 assigned to it that abuts against the bridge section 20 of this ligature clip on the outside when the cartridge is filled.

Holding tongues 38 projecting inwards in a similar manner are moulded on the inside surface 37 of the cover 11 facing the ligature clips 5, their free edges 39, like the front edge 35 of holding tongues 34, abutting against the bridge sections 20 of the ligature clips 5, and for this purpose a cutout 40 adapted to the shape of the bridge sections 20 of the ligature clips 5 is also provided in these free edges. Here, the number and spacing of the holding tongues 38 also correspond to the number and spacing of the ligature clips 5 in the cartridge 8 when this is filled.

The holding tongues 34 and 38 cooperate so that while the ligature clips can be slid past the holding tongues in distal direction, which in this case spring into the first transport element 28 or the cover 11, the holding tongues prevent a displacement of the ligature clips 5 in proximal direction, since they abut against the bridge sections 20 of the ligature clips 5. If the first transport element 28 and the cover 11 are displaced relative to one another, e.g. by the first transport element 28 being displaced relative to the cover 11 by one cartridge spacing in distal direction and then in proximal direction, then during advance of one of the two parts the ligature clip 5 is advanced by one position in the cartridge in distal direction, and during the return movement of the parts the ligature clip remains in the advanced position and the holding tongues slide past the advanced ligature clip. This occurs in the same manner with all ligature clips in the cartridge, so that when the first transport element 28 slides forward and back relative to the cover 11 in this manner all the ligature clips 5 in the cartridge 8 are displaced by one position in distal direction.

A feed member 41, which has a plane base surface 42 and two side faces 43 and 44 projecting perpendicularly therefrom towards the same side, from which guide projections 45 facing one another and running parallel to the base surface 42 protrude, is arranged in the cartridge 8 to proximally adjoin the ligature clips 5 accommodated in the cartridge 8. This feed member 41 is slid over the two transport elements 28, 29 so that these penetrate into the inside area of the feed member 41 and thus abut flat against the base surface 42, while they are guided on the opposite side by the guide projections 45. Thus, in the region in which the transport elements 28 and 29 penetrate into the feed member 41, this feed member 41 assumes guidance of the transport elements 28, 29 that in distal direction from the feed member 41 is performed by the ligature clips 5, which the transport elements 28 and 29 pass through in the region of the longitudinal slit 21. As the cartridge 8 empties, the feed member 41 follows the ligature clips and increasingly replaces their guidance until the cartridge is completely empty and the transport elements 28, 29 are guided exclusively by the feed member 41, which then occupies the position of the ligature clips at the beginning of the advancing process.

Advancing of the feed member 41 can be achieved by the feed member 41 being advanced in distal direction by a spring (not shown in the drawing) and as a result always being supported against the last ligature clip in the cartridge. This support can occur by abutment of the distal end of the feed member 41 against the bridge section 20 on the ligature clip 5 furthest to the rear in the cartridge 8.

In another embodiment, which is shown in the drawing, cutouts 46 are provided in the base surface 42, into which the holding tongues 34 of the first transport element 28 and the holding tongues 38 of the cover 11 engage in exactly the same way as they do between adjacent ligature clips, so that in this way when the first transport element 28 is slid forward and back in relation to the cover 11 the feed member 41, in the same way as the ligature clips 5, is also respectively advanced in distal direction by one ligature clip position. Therefore, also in relation to this, the feed member 41 forms a body that replaces the ligature clips in the cartridge when these are ejected stepwise out of the cartridge.

In the exemplary embodiment shown in the drawing, the number and spacing of the holding tongues 34 and the holding tongues 38 are selected to correspond with the number and spacing of the ligature clips in the cartridges. However, it would also be possible to provide a smaller number of holding tongues, e.g. the spacing of the holding tongues could be double the spacing of the ligature clips in the cartridge. This would have the advantage that lower friction forces occur when the holding tongues slide along the ligature clips. In such a configuration, holding tongues do not act on each ligature clip during advance, so that only every second ligature clip is advanced by the transport element 28 and the cover 11. The rest of the ligature clips are then only advanced by the following ligature clip being supported on them and entraining these in distal direction when it is advanced by the holding tongues.

However, in the case of the last ligature clip, i.e. the very last in proximal direction, this does not always work when there is a holding tongue only in every second position for the advance. In this case, the advance of the respective last ligature clip is taken over by the feed member 41 that is supported against this ligature clip furthest to the rear and is advanced stepwise in distal direction by the holding tongues. Naturally, it is also necessary that the feed member 41 then has at least two cutouts 46, into which holding tongues can engage, so that there is always one holding tongue engaging into the feed member, even if the holding tongues have double the spacing of the ligature clips in the cartridge.

The spacing of the holding tongues could also be even greater, e.g. one holding tongue pair effecting the advance could be provided for only every third ligature clip. Then, the ligature clips advanced by the holding tongues respectively push two ligature clips in front of them.

The first transport element 28 has holding tongues 34 for all ligature clips 5 in the cartridge 8 with the exception of the ligature clip 5 furthest forward adjacent to the discharge end 27. Thus for this clip it is the second transport element 29 and not the first transport element 28 that assures its advance.

Figure 13:
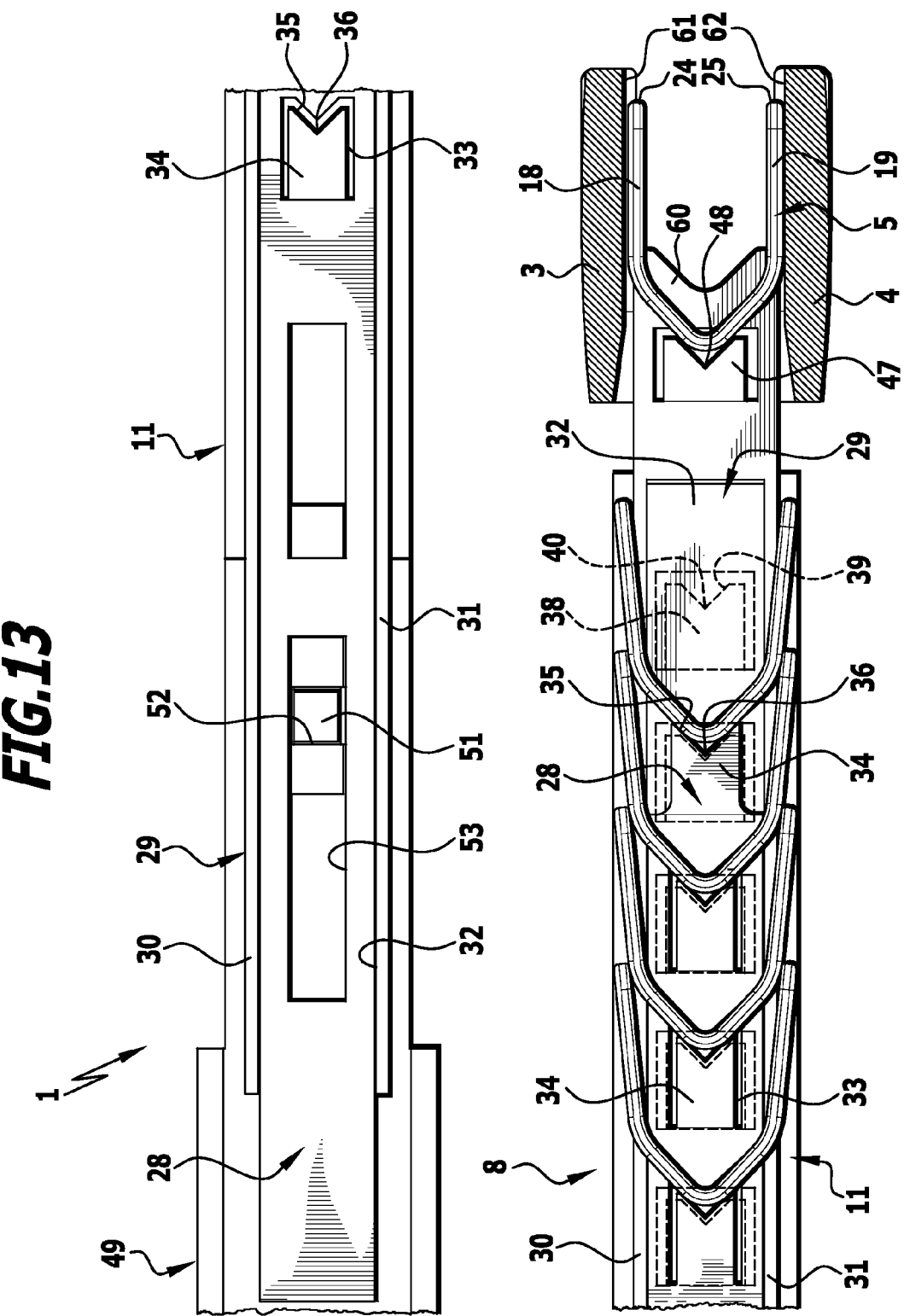
FIG. 13 is a view similar to FIG. 12 with the ligature furthest forward fully advanced between the clamping jaws.
Figure 14:
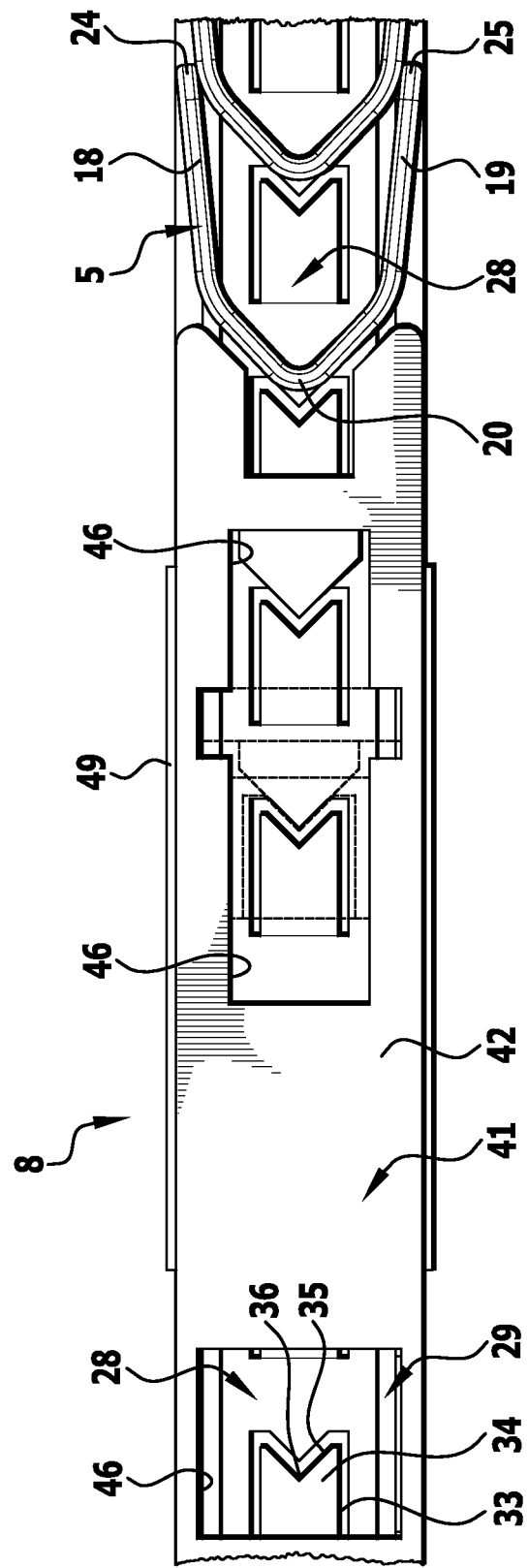
FIG. 14 is a side view of the transport elements and a feed member slid over it.

The second transport element bears a holding tongue 47 at its distal end that, in a similar manner to holding tongue 34, is cut out of the second transport element 29 by a C-shaped separation cut and laterally projects therefrom. This has a cutout 48 on its front edge that abuts against the bridge section 20 of the ligature clip 5 furthest forward and advances this in distal direction when the second transport element 29 is advanced in distal direction. During this advance the ligature clip 5 furthest forward is slid through the discharge end 27 between the two clamping jaws 3, 4 until the ligature clip 5 is fully positioned between these clamping jaws 3, 4, so that the legs 18, 19 abut against the clamping jaws 3, 4 over their entire length (FIG. 13).

The feed path for the ligature clip 5 furthest forward from the position furthest forward in the cartridge to the placement position between the clamping jaws 3, 4 is greater than the feed path that the ligature clips follow inside the cartridge when they are advanced by one respective step. For this reason, the advancing movement is not performed by means of the first transport element 28, but by means of the second transport element 29.

To enable the first transport element 28 and the second transport element 29 to be alternately slid forward in distal direction and back in proximal direction for advance of the ligature clips 5, a slide 49 is disposed on the cartridge to be displaceable in the longitudinal direction, i.e. to adjoin the cover 11 in proximal direction. The slide 49 bears a projection 50, which projects into the barrel 2 and is connected to one of the transmission members there that can be slid forward and back from the instrument handle (not shown in the drawing) in the longitudinal direction of the barrel and in so doing also accordingly slide the slide forward and back. The slide bears a laterally protruding projection on its distal end that acts as entrainment means 51 and engages into a recess 52 of the second transport element 29 as well as an opening 53 of the first transport element 28. In this case, the recess 52 surrounds the entrainment means 51 on all sides, so that a displacement of the entrainment means during the displacement of the slide 49 is transmitted in the same way to the second transport element 29. In contrast, the opening 53 is configured in the form of a longitudinal slit, so that the entrainment means 51 can be displaced along the opening 53 without displacing the first transport element 28 in the same way. An entrainment only occurs when the entrainment means 51 strikes against one of the end edges of the opening 53, i.e. the first transport element 28 is only displaced during a portion of the displacement movement of the entrainment means 51 in distal direction and during the return movement in proximal direction. Thus, feed paths of different lengths can be achieved with the same entrainment means 51, namely a long feed path for the second transport element 29 that corresponds to the feed path of the slide during its forward and back movement, and a short feed path for the first transport element 28, which feed path corresponds to the spacing of adjacent ligature clips in the cartridge.

In the exemplary embodiment shown in the drawing, the second transport element 29 projects into the space 21 between the sections 22, 23 of the ligature clip furthest forward with its front end 60, so that the ligature clip furthest forward is thus provided with a lateral guidance during the entire advance. During this advance, the ligature clip 5 furthest forward is pushed out of the cartridge 8 between the adjoining clamping jaws 3, 4. As can be seen from the representation in FIG. 16, the longitudinal direction of the clamping jaws 3, 4 is inclined, if necessary, in relation to the longitudinal direction of the ligature clips in the cartridge and thus in relation to the direction of advance of the ligature clips in the cartridge, so that a curved feed path results between the discharge end of the cartridge 8, on the one hand, and the clamping jaws 3, 4, on the other. The transport element 29 configured as an elastic metal flat strip can readily follow this curved feed path and thus also guides the ligature clip furthest forward along this feed path that is not rectilinear but curved as far as in between the clamping jaws 3, 4.

As is evident from the illustration in FIG. 13, the ligature clip furthest forward is also provided with a lateral guidance in the region of the clamping jaws 3, 4, since these clamping jaws 3, 4 have longitudinal grooves 61, 62 running in their longitudinal direction, into which the legs 18, 19 of the ligature clip 5 penetrate. It is also clear from the illustration in FIG. 13 that the spacing of the two clamping jaws 3, 4 is selected so that the legs 18, 19 of the ligature clip 5 that diverge slightly in the cartridge are elastically pressed together, so that the legs 18, 19 run substantially parallel to one another. As a result, the legs 18, 19 abut against the base of the guide grooves 61, 62 with their outer surface and clamping or friction forces result there, so that after sliding in between the two clamping jaws 3, 4 the ligature clip 5 furthest forward is held between these in a clamped or friction-tight fit, even when the transport element 29 is withdrawn again after reaching the feed position furthest forward. This ensures that the ligature clip 5 furthest forward cannot be unintentionally displaced in the longitudinal direction of the guide grooves 61, 62.

In the exemplary embodiments described in FIGS. 1 to 16 the ligature clips 5 are guided through the guide part 10, its base 12, side walls 13, 14 and the guide bars 16, 17.

Figure 16:
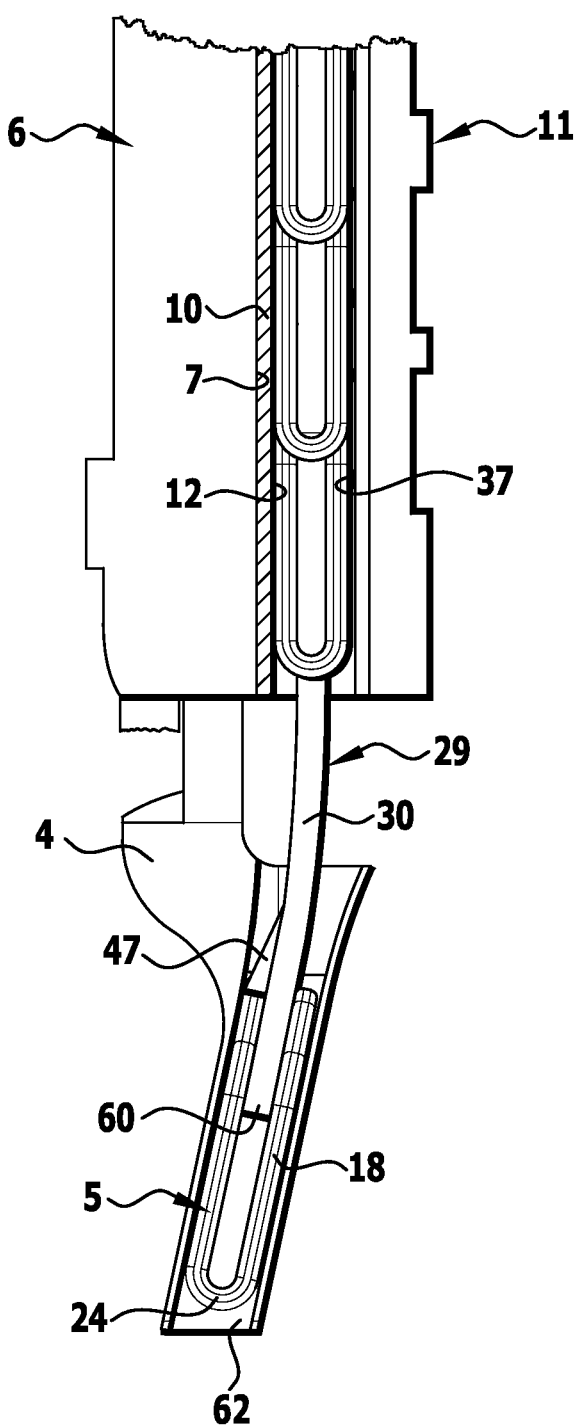
FIG. 16 is a plan view onto the discharge end of the cartridge and the adjoining clamping jaws.
Figure 17:
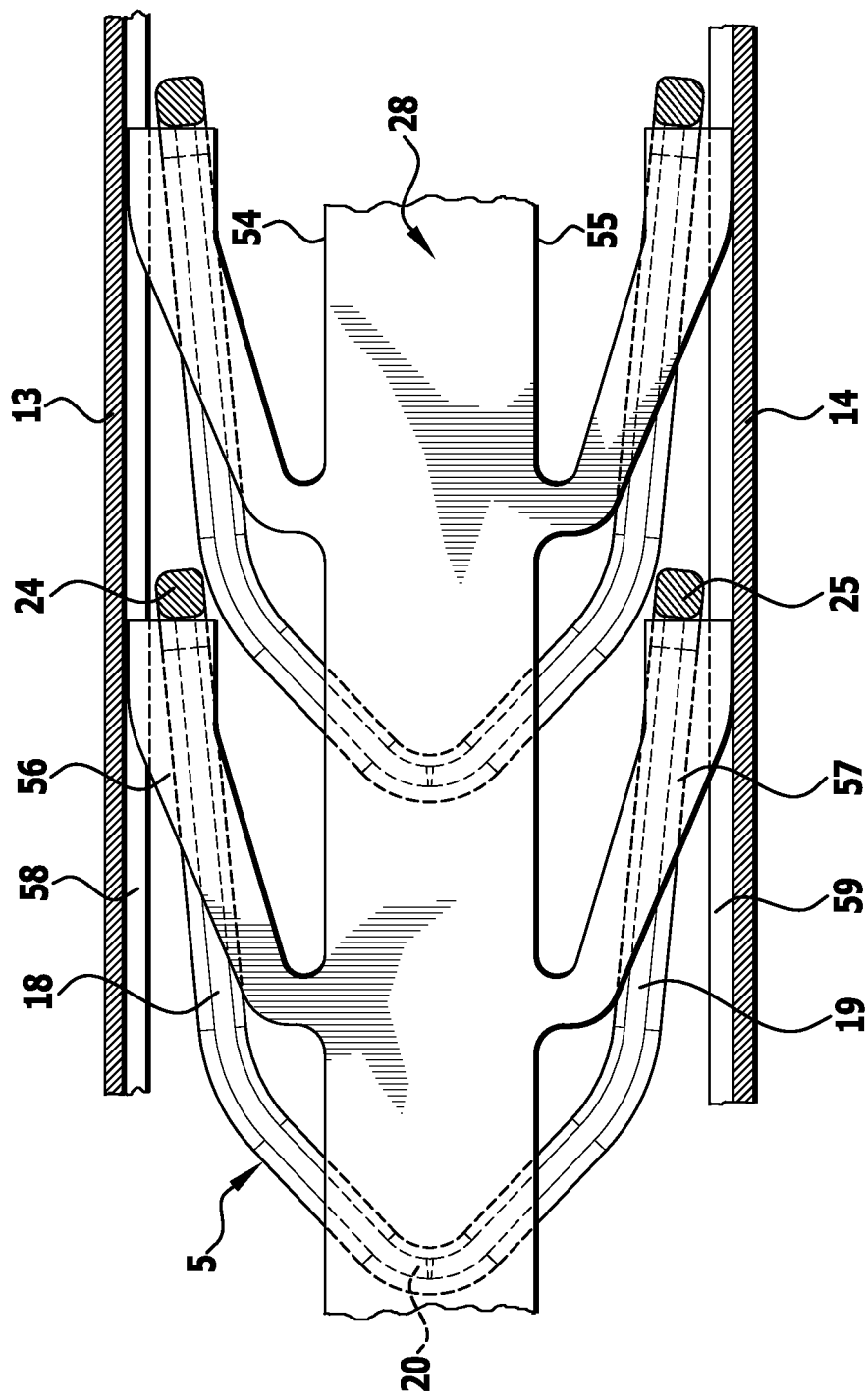
FIG. 17 is a side view of a further exemplary embodiment of a transport element for advancing ligature clips.

A slightly modified type of guidance is provided in the exemplary embodiment of FIG. 16. In this exemplary embodiment the first transport element 28 bears upwardly and downwardly projecting arms 56, 57 on its upper edge 54 and on its lower edge 55 and lying in the plane of the first transport element 28, said arms protruding upwards and downwards and engaging through the longitudinal slit 21 of the ligature clips 5. Guide grooves 58, 59 are provided in the side walls 13, 14, which run in the longitudinal direction and respectively open to the opposite side wall and into which the arms 56, 57 project and are thus guided in these guide grooves 58, 59 in the longitudinal direction of the guide part 10. As a result, they also guide the ligature clips 5, through which the arms pass in the region of their longitudinal slits 21. At the same time, the arms 56, 57 are supported at their free ends against the connections 24, 25 of the ligature clips 5, so that the ligature clips 5 are entrained when the transport elements 28 are displaced in distal direction. Therefore, holding tongues 34 are not necessary in the first transport element 28.

The arms 56, 57 can be bent elastically relative to one another, so that they leave the guide grooves 58, 59 and are also pivoted into the inside area of the ligature clips 5, so that they no longer pass through the longitudinal slit 21 of the legs 18, 19. In this position the first transport element 28 can be displaced in proximal direction and the arms 56, 57 then slide past the connections 54, 55 of the following ligature clip 5 until when pivoting resiliently out they abut against these connections 34, 35 again. The arms 56, 57 thus assume a double function, namely firstly the function of guiding the ligature clips in the guide part 10 and secondly the function of the holding tongues 34, i.e. the elastically deformable entrainment elements for advancing the individual ligature clips.

In order to prevent all the arms 56, 57 from springing out of the guide grooves 58, 59 and being pivoted into the inside area of the ligature clips 5, the spacings of the arms 56, 57 can be selected to be different in the longitudinal direction, i.e. not to correspond exactly to the spacing of the ligature clips, so that the arms 56, 57 pivot in at different locations of the first transport element 28 with different positions of the transport element 28, and then there are always arms 56, 57 remaining in engagement with the guide grooves 58, 59, so that the guidance is maintained.

In the exemplary embodiments described so far, holding tongues 34, 38, 47 were arranged on the transport elements 28, 29 and on the cartridge 8 as holding projections, which can be resiliently pivoted into the plane of the transport elements or the cover 11 and past which the ligature clips can respectively slide in one direction, whereas they are hindered from sliding past the holding projections in the opposite direction.

Figure 18:
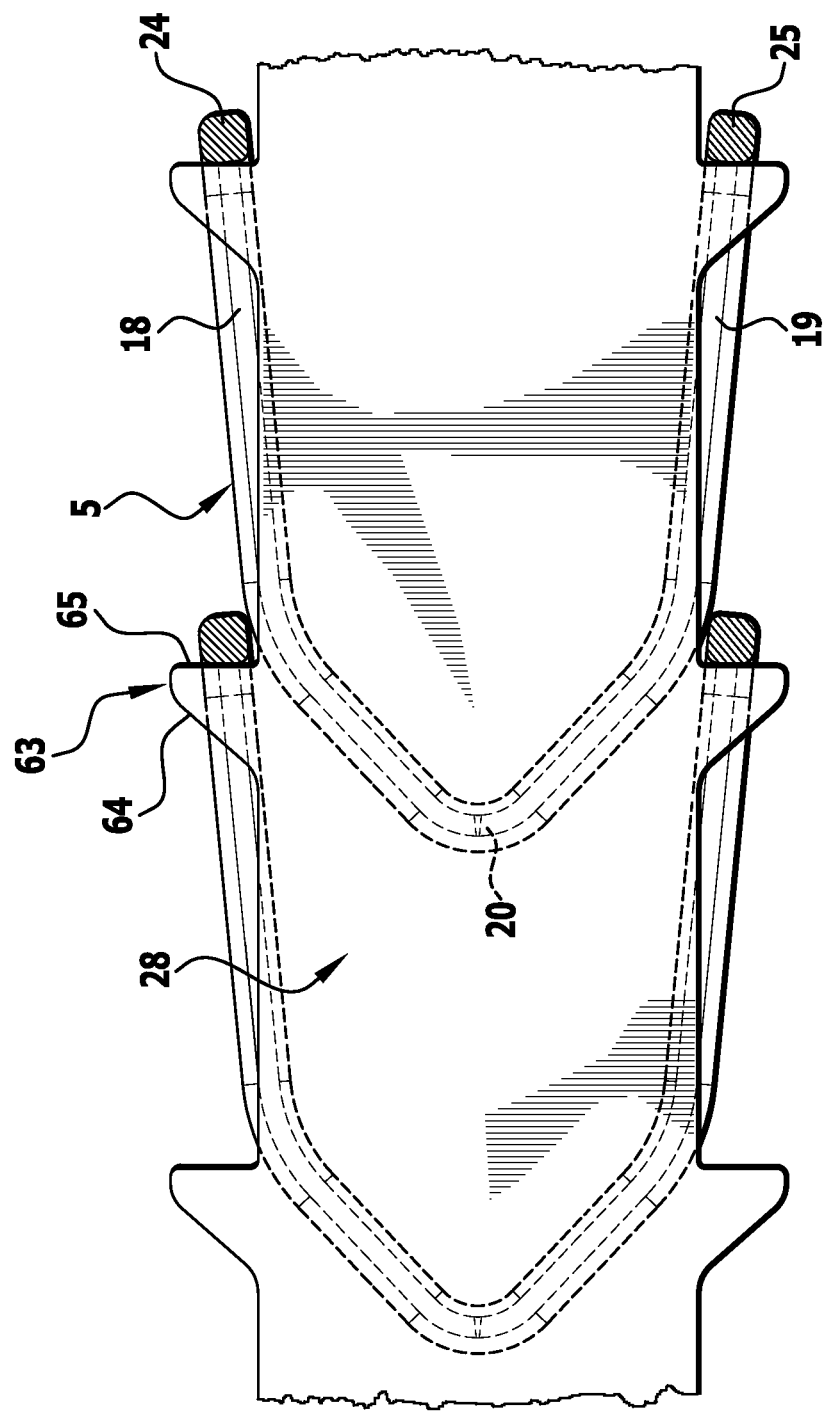
FIG. 18 is a side view of a transport element with saw tooth-like holding projections and with ligature clips abutting against them.
Figure 19:
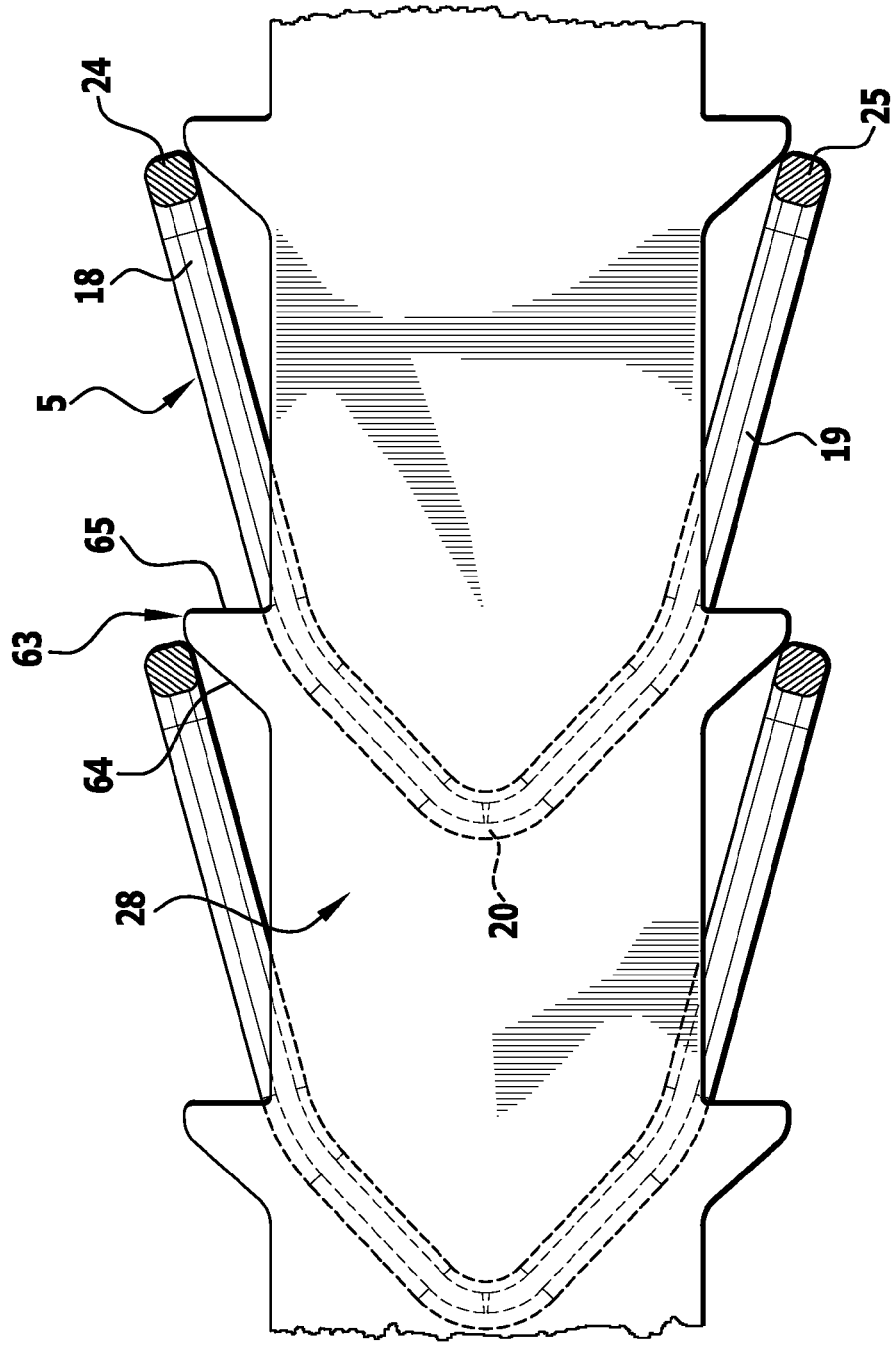
FIG. 19 is a view similar to FIG. 18 with expanded ligature clips when sliding past a holding projection.
Figure 20:
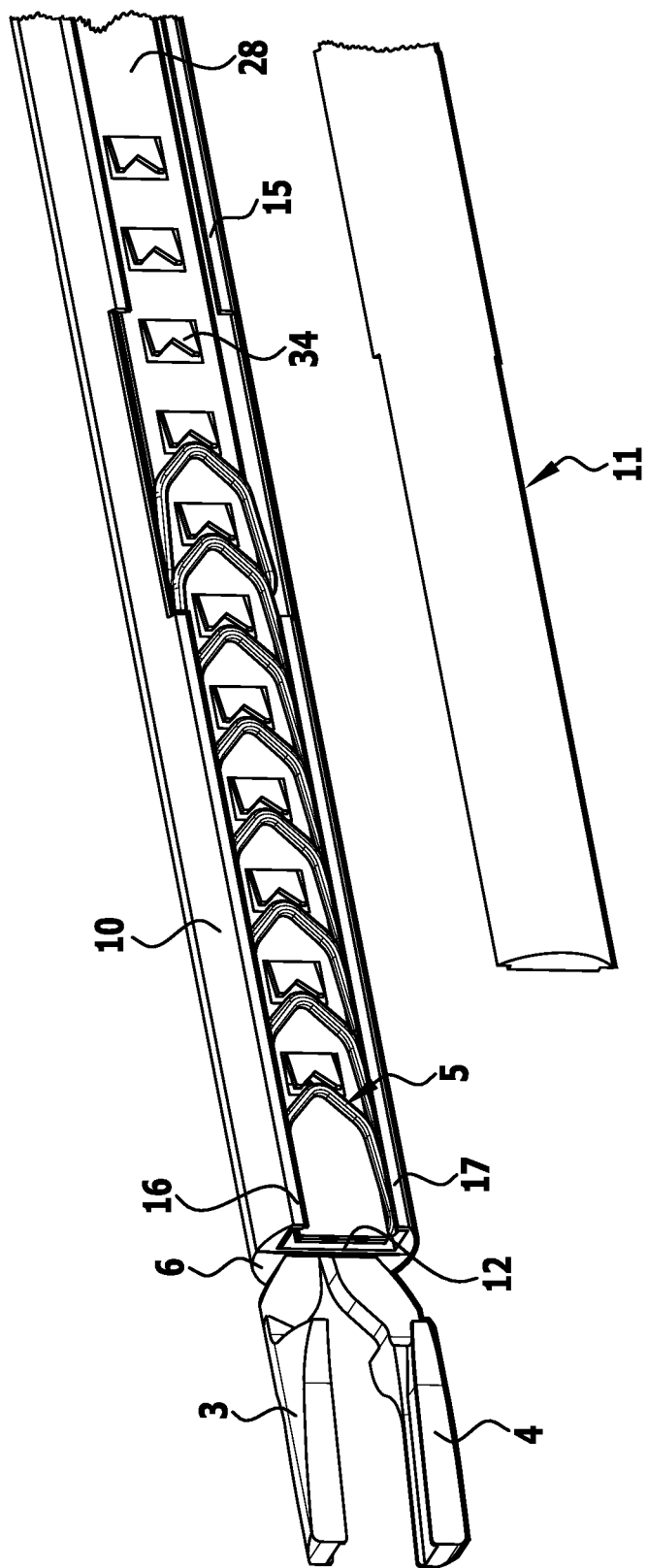
FIG. 20 is a perspective view of a further preferred exemplary embodiment of a surgical placement instrument with a strip-like transport element and a strip-like retaining element in the space between the ligature clips received in the cartridge with cover removed.
Figure 21:
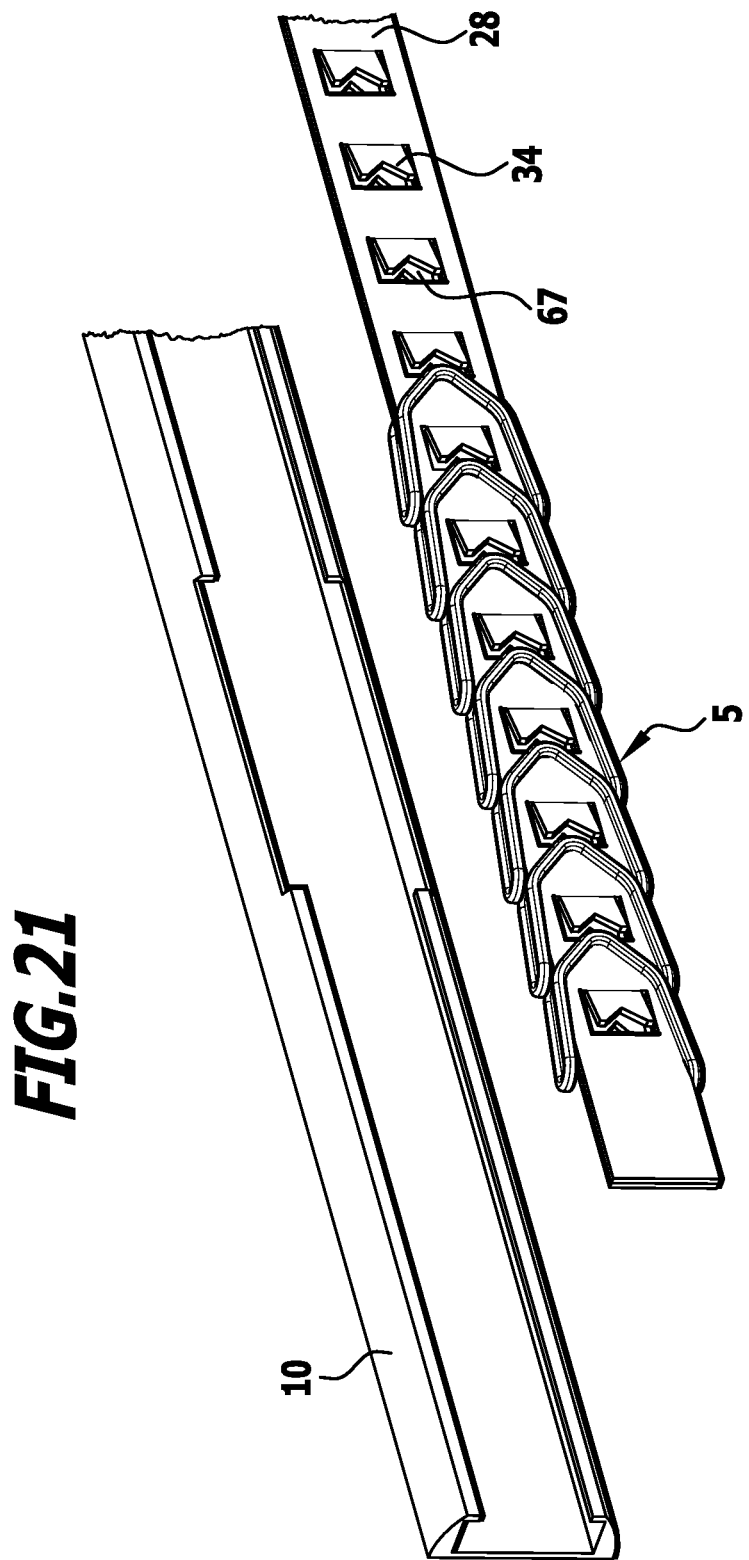
FIG. 21 is a perspective view of the transport and retaining elements removed from the guide part of the cartridge with ligature clips engaging over these.
Figure 22:
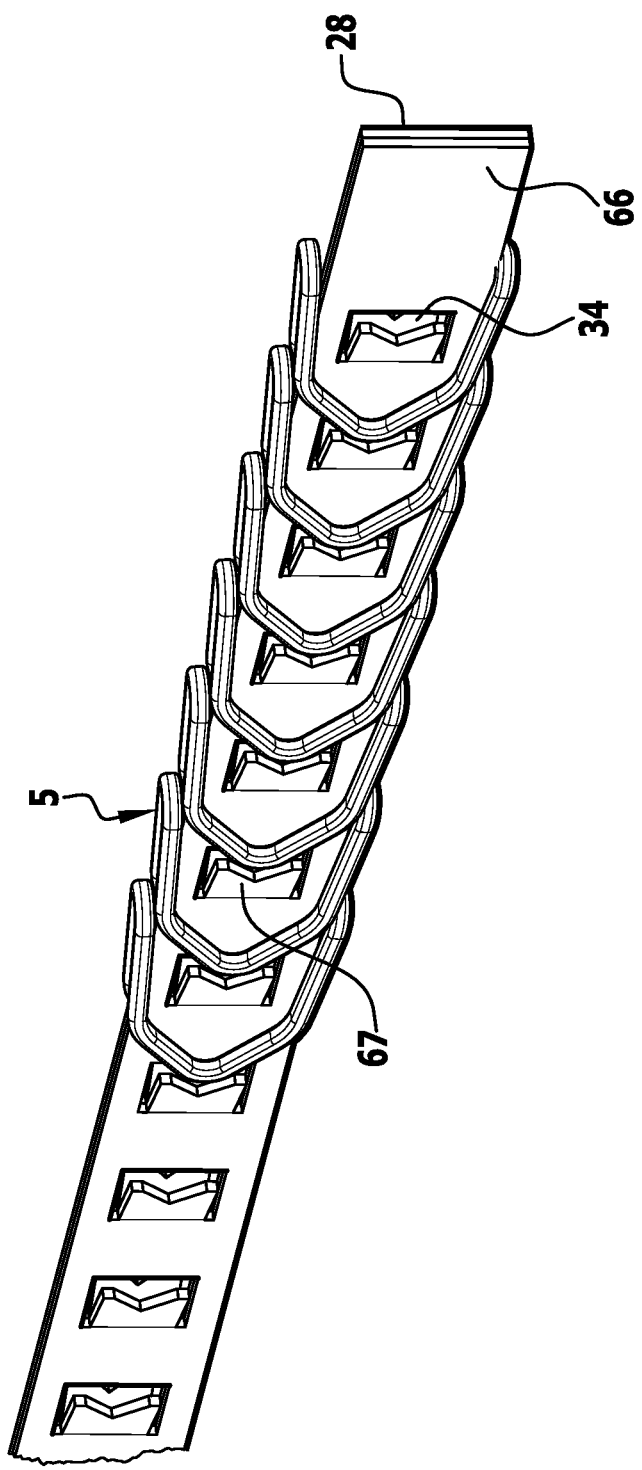
FIG. 22 is a perspective view of the transport element and the retaining element of FIG. 21 from the opposite side.

Configurations are also conceivable, in which the holding projections are not configured as resilient holding tongues, but as non-deformable holding projections 63 that project upwards and downwards on the longitudinal edges of the transport elements 28, 29 (FIGS. 18 and 19). These holding projections 63 are saw tooth-shaped in cross-section and have an upwardly sloping slide surface 64 on one side and an abutment surface 65 running perpendicularly to the direction of advance on the opposite side. When these holding projections 63 approach the connections 24, 25 of the ligature clips 5, by means of which the adjacent sections 22, 23 of the legs 18, 19 are connected to one another, then these connections 24, 25 slide on the slide surfaces 64, so that the legs 18, 19 are elastically bent apart, as is shown in FIG. 19. The holding projections 63 can thus slide past the connections 24, 25. However, if the connections 24, 25 approach this holding projection 63 from the other side, they abut against the abutment surfaces 65, which run perpendicularly to the direction of advance and on which no sliding can therefore occur. It is thus possible to slide the connections 24, 25 further past the holding projections 63. It thus becomes clear that in this configuration, as with the elastic holding tongues on the transport elements 28, 29, the ligature clips can only slide past the holding projections 63 in one direction and not in the opposite direction. While the elasticity of the holding tongues is used in the exemplary embodiment of FIGS. 1 to 15, the elasticity of the legs 18, 19 of the ligature clips 5 is used in the exemplary embodiment of FIGS. 18 and 19 to achieve this one-way displaceability.

It is naturally essential that the legs 18, 19 in the cartridge are guided such that they cannot spring out so that the connections 24, 25 can be displaced beyond the holding projections 63.

In the exemplary embodiment described so far the ligature clips are protected against sliding back against the direction of advance by the holding tongues or holding projections located on the cover 11 of the cartridge 8.

In contrast, in a modified exemplary embodiment the ligature clips are held back by holding projections, which are not arranged directly on the housing 9 of the cartridge 8, but on a strip-shaped retaining element 66, which is configured in a similar manner to that described above on the basis of the second transport element 29 and abuts flat against the first transport element 28. Like the second transport element 29, it can be received in a receiving space 32 of the first transport element 28 and replaces this. However, in contrast to the second transport element 29, the retaining element 26 is connected to the housing 9 to be non-displaceable in the direction of advance, which can be achieved by connecting elements not shown in the drawing. Like the first transport element 28, the retaining element 66 bears elastic holding tongues 67, which are arranged in the same way as the holding tongues 38 on the cover 11 of the housing in the configurations described above. Thus, these holding tongues 67 act like the holding tongues 38, i.e. they prevent a displacement of the ligature clips against the direction of advance. In this case, the holding tongues 38 do not have to be provided on the cover 11, the retaining function being assumed by the holding tongues 67 of the retaining element 66.

In this embodiment all the ligature clips must be advanced by the first transport element 28, i.e. including the ligature clip furthest forward.

Figure 23:
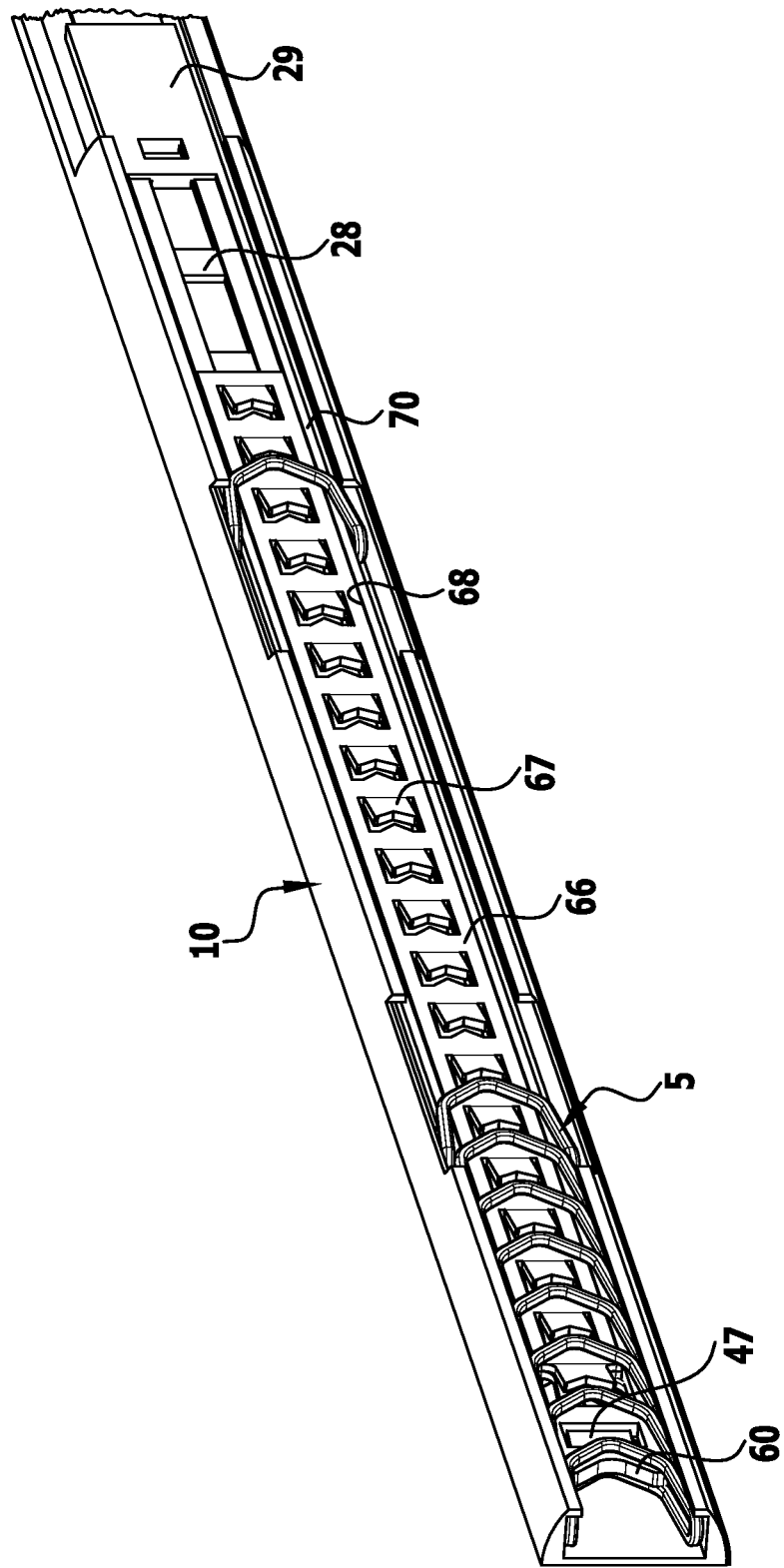
FIG. 23 is a view of a further preferred exemplary embodiment of a surgical placement instrument with two transport elements for the ligature clips and a retaining element received in the space between the ligature clips.
Figure 24:
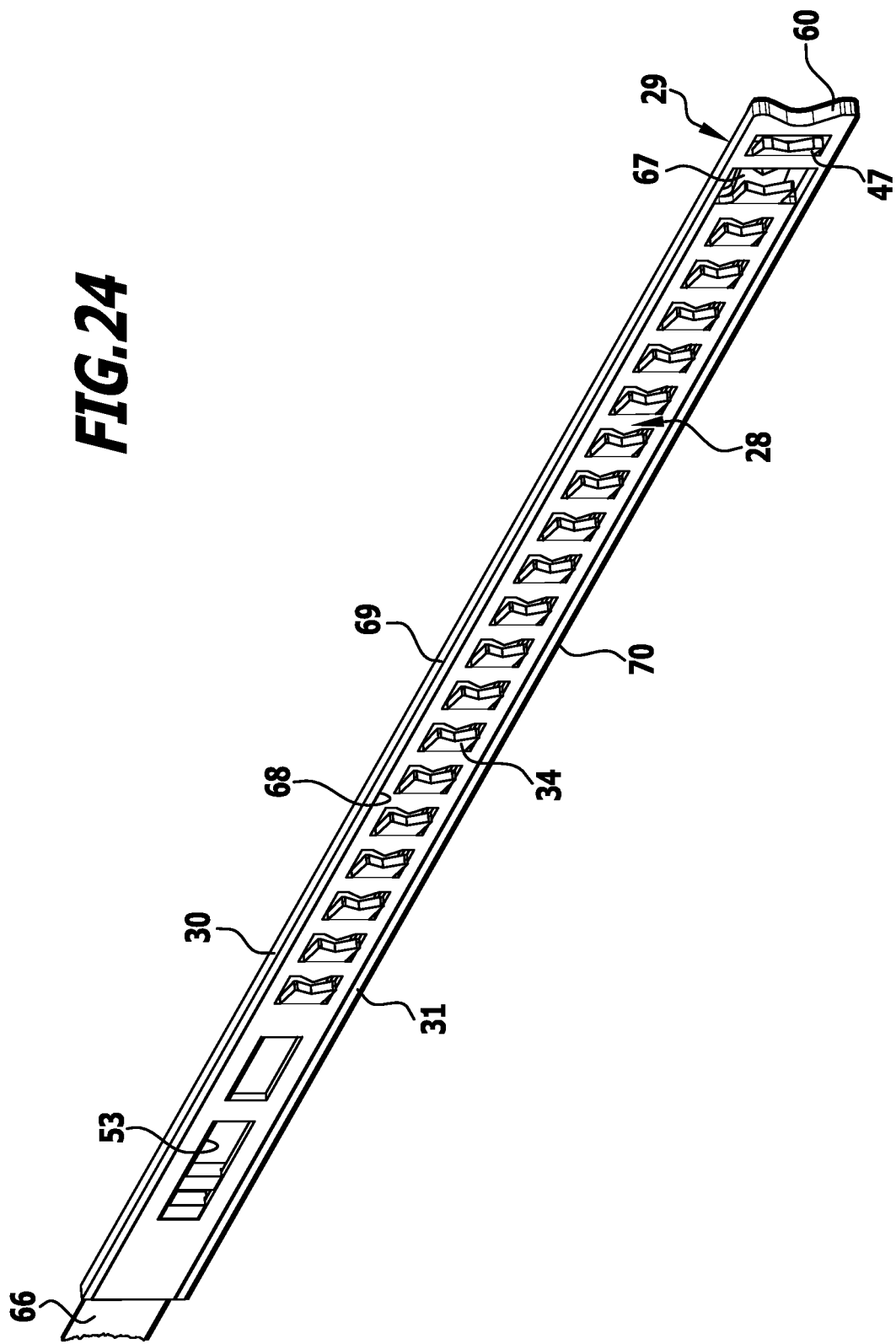
FIG. 24 is a perspective view of the retaining element and the two transport elements of the exemplary embodiment of FIG. 23.
Figure 25:
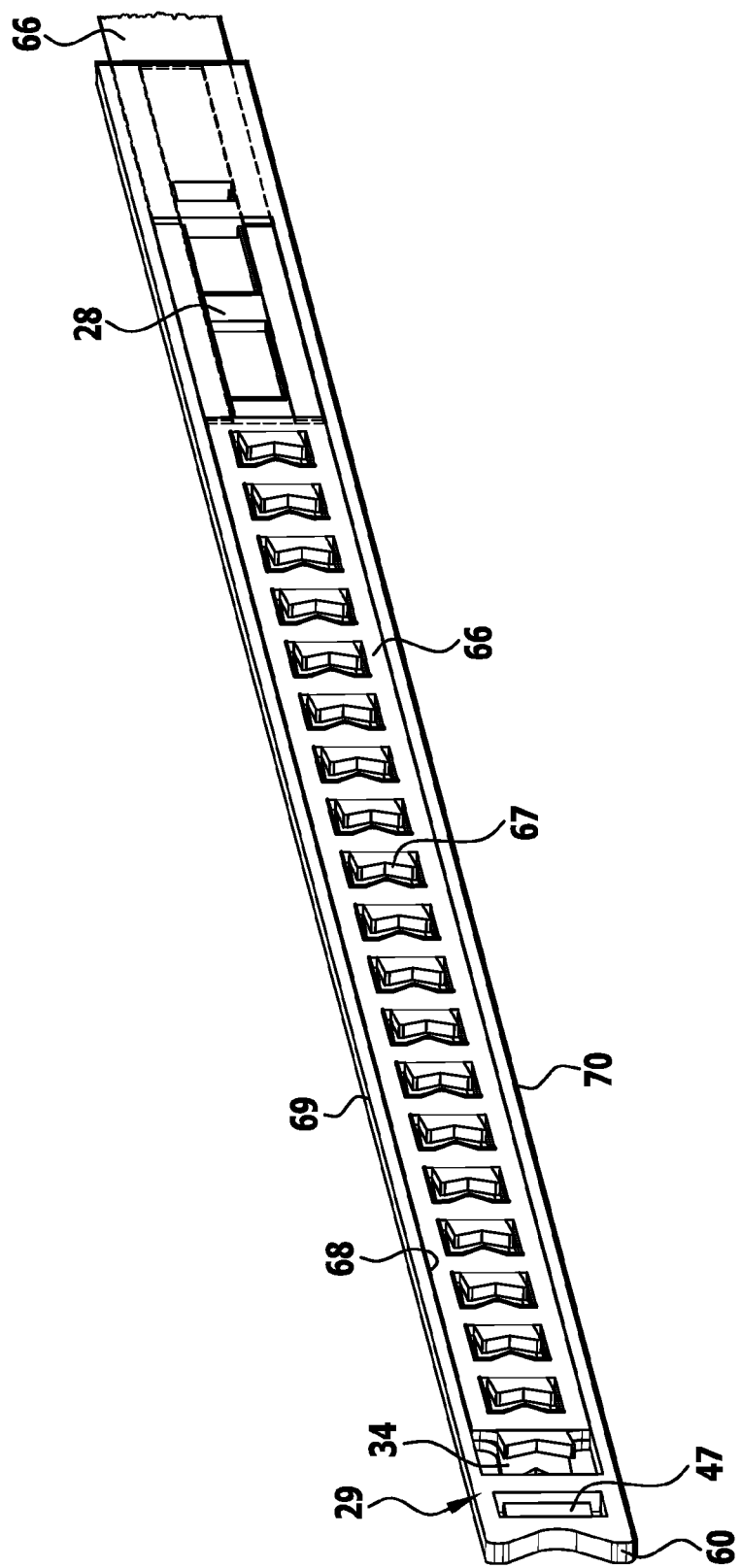
FIG. 25 is a view similar to FIG. 24 viewed from the opposite side.

It would be possible in principle to not only accommodate two strip-like elements in the space 21 between the ligature clips 5, i.e. two transport elements 28, 29 or a transport element 28 and a retaining element 66, but three such strip-like elements could also be provided, wherein two transport elements and one retaining element are provided. Such a configuration is shown in FIGS. 23 to 25. In this case, a second transport element 29 is used that has an opening 68 extending over a large portion of its length, in which the first transport element 28 and the retaining element 66 are arranged. The front end and the rear end of the second transport element 29 are thus only connected to one another by means of narrow webs 69, 70 running parallel to one another. Otherwise, the described parts have the same configuration and the same function as those explained on the basis of the above exemplary embodiments.

Figure 26:
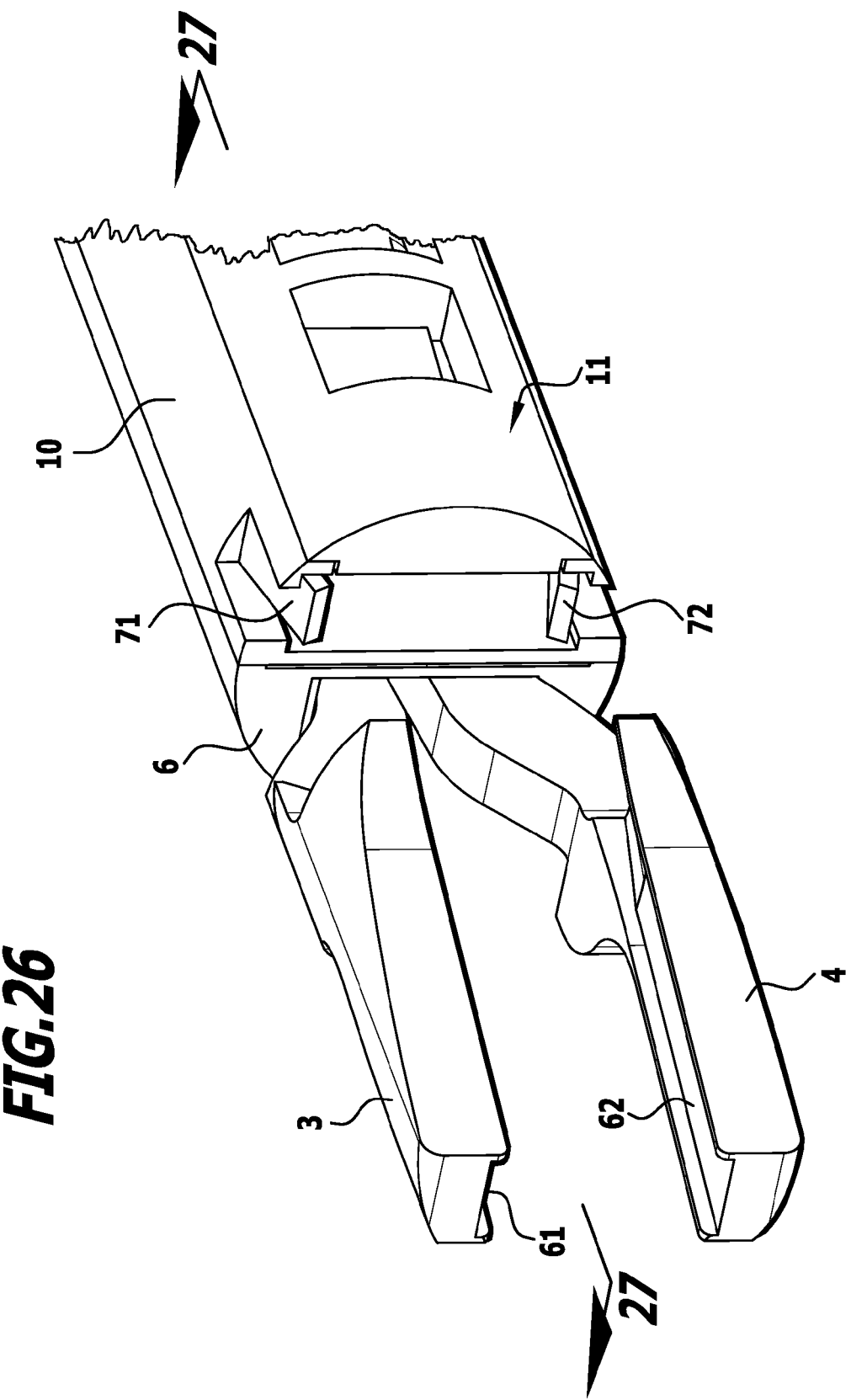
FIG. 26 is a perspective view of the cartridge and the clamping jaws in the region of the discharge end of the cartridge with clamping elements pivoted into the feed path of the ligature clips.
Figure 27:
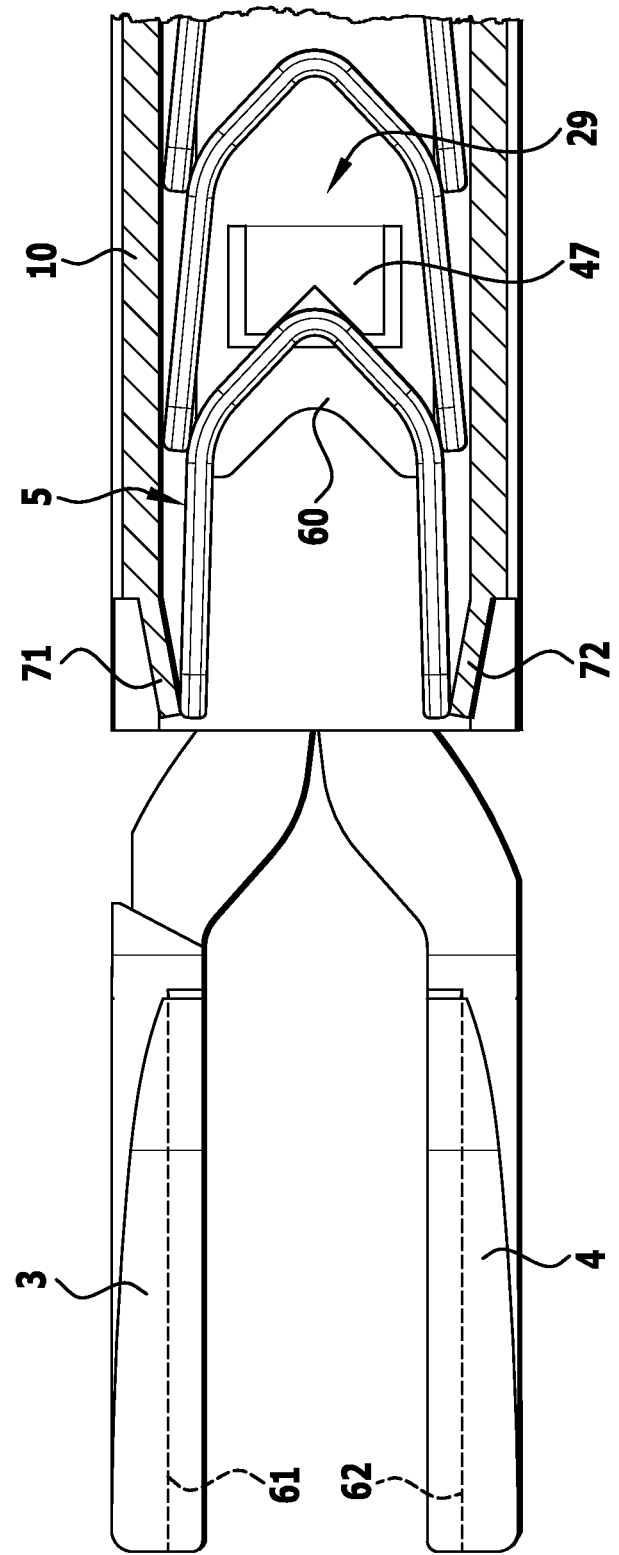
FIG. 27 is a view in longitudinal section taken along line 27-27 of FIG. 26.

To secure the ligature clip furthest forward during advance out of the cartridge 8 between the clamping jaws 3, 4, besides the clamping force exerted by the clamping jaws 3, 4 or also independently thereof, additional clamping elements can be used that abut against the ligature clip and prevent an unintended displacement of the advanced ligature clip by friction forces. In the exemplary embodiment of FIGS. 26 and 27, clamping lugs 71, 72 projecting into the feed path of the ligature clip 5 are moulded on the guide part 10 at the end of the side walls 13, 14 on the discharge side and can be bent elastically outwards, so that they are pushed out of the feed path of the ligature clips. When the ligature clip furthest forward advances out of the cartridge between the clamping jaws 3, 4, the clamping lugs 71, 72 abut against the outer surfaces of the legs 18, 19 and are elastically pivoted outwards by the advanced ligature clip 6, in which case the clamping lugs 71, 71 press onto the outer surfaces of the legs 18, 19 and thus generate a clamping or friction force, which protects the ligature clip 5 from an unintended displacement along the feed path. This applies in particular in the transition region between the exit of the cartridge and the clamping jaws 3, 4.

Figure 28:
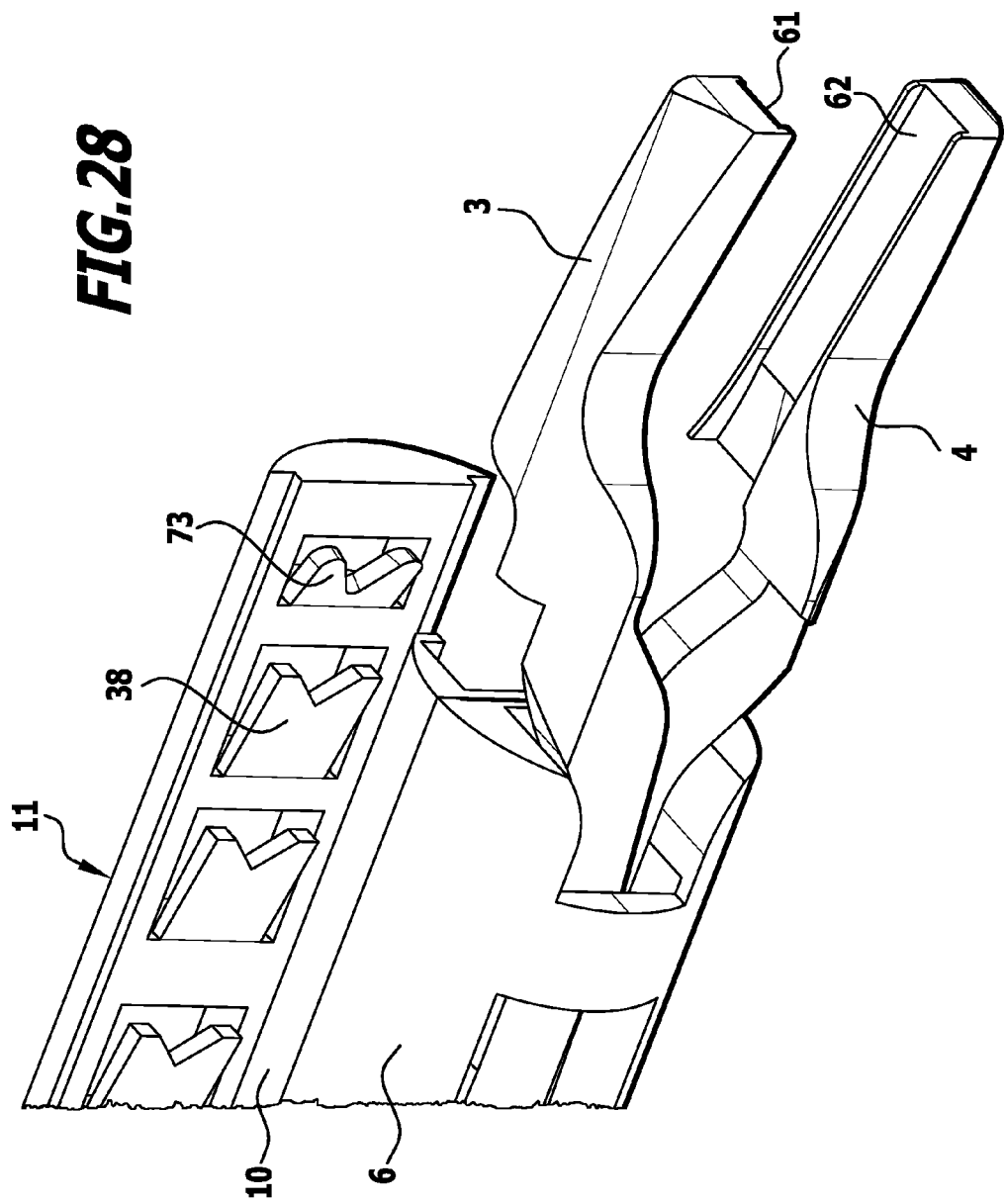
FIG. 28 is a perspective view of the discharge end of the cartridge and the clamping jaws with cover removed and with a clamping element on the cover projecting into the feed path of the ligature clips.
Figure 29:
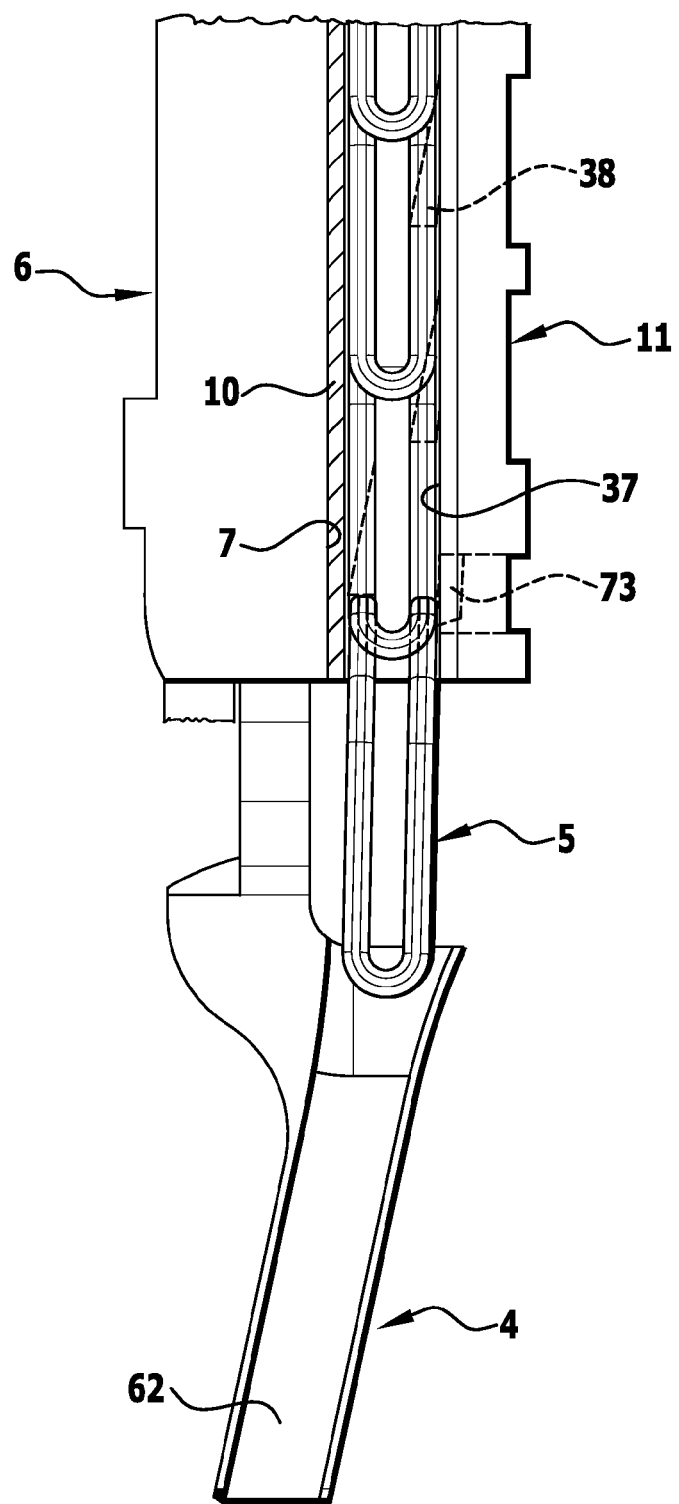
FIG. 29 is a plan view onto the discharge end of the cartridge and the clamping jaws of FIG. 28 with a guide part cut in longitudinal direction.

In the exemplary embodiment of FIGS. 28, 29 an elastic clamping tongue 73 is moulded on the cover 11 in a similar manner, i.e. on the end of the cover 11 on the discharge side, and abuts laterally against the legs 18, 19 and is pivoted from these into the plane of the base 12 when the ligature clip 5 slides past. This clamping tongue 73 therefore also clamps against the ligature clip 5 and protects this from an unintentional displacement along the feed path.

What is claimed is:

1. Cartridge with a plurality of C-shaped ligature clips, comprising:
a housing accommodating the ligature clips, the ligature clips being arranged in a row one behind the other and parallel to one another, and
at least one transport element, which can be slid forward and back relative to the housing in a direction of the row and which when sliding forward relative to the housing causes at least one ligature clip to advance towards a discharge end of the cartridge,
wherein:
the ligature clips each have two legs connected by means of a bridge section and are divided by a longitudinal slit into two adjacent sections, which are connected to one another in a region of free ends of the legs, and
the at least one transport element passes through the ligature clips arranged in a row in a space between the two adjacent sections of the ligature clips.

2. Cartridge according to claim 1, wherein the at least one transport element abuts against inner sides of the adjacent sections of the ligature clips and results in a mutual guidance between the ligature clips and the at least one transport element.

3. Cartridge according to claim 1, wherein each of the at least one transport elements comprises a flat strip.

4. Cartridge according to claim 1, wherein the ligature clips are supported in the housing to be displaceable in the direction of the row by a guide means.

5. Cartridge according to claim 4, wherein guide members of the guide means are arranged on the housing and the ligature clips are in guiding contact with the guide members.

6. Cartridge according to claim 4, wherein guide members of the guide means are arranged on the housing, and guide elements arranged on the at least one transport element and passing through the space between adjacent sections of the ligature clips are in guiding contact with the guide members.

7. Cartridge according to claim 6, wherein:
the guide elements of the at least one transport element are resilient, so that the ligature clips can be slid past them, the guide elements are elastically displaceable into an inner space between the legs of the ligature clips.

8. Cartridge according to claim 6, wherein spacings of adjacent guide elements of the at least one transport element are different from a spacing of adjacent ligature clips in the housing or from a multiple of the spacing of the adjacent ligature clips in the housing.

9. Cartridge according to claim 1, wherein the ligature clips are guided loosely relative to at least one of the at least one transport element and the housing.

10. Cartridge according to claim 1, wherein holding projections elastically deformable between an abutment position and a release position are arranged on the housing or a part connected to the housing and on the at least one transport element, and in the abutment position said holding projections abut against the ligature clips and prevent a displacement of the ligature clips against a direction of advance and are deformed by the ligature clips during their advance into the release position, in which the ligature clips can be moved past the holding projections in the direction of advance.

11. Cartridge according to claim 10, wherein the number and spacings of the holding projections, with the exception of the ligature clip furthest forward in the direction of advance, are equal to the number and spacings of the ligature clips in a filled cartridge.

12. Cartridge according to claim 10, wherein spacings of adjacent holding projections are different.

13. Cartridge according to claim 10, wherein only one respective holding projection is provided on the at least one transport element and on the housing or the part connected to the housing for each group of a plurality of the ligature clips arranged in a row one behind the other.

14. Cartridge according to claim 10, wherein there is arranged adjacent to the at least one transport element in the space between the adjacent sections of the ligature clips, a retaining element, which is connected to the housing and is non-displaceable relative to the housing in the direction of the row, and which comprises the elastically deformable holding projections.

15. Cartridge according to claim 14, wherein the at least one transport element and the retaining element are configured as flat strips abutting flat against one another.

16. Cartridge according to claim 15, wherein the at least one transport element has a longitudinal groove, in which the retaining element is received in a guided manner.

17. Cartridge according to claim 10, wherein the holding projections are arranged on the at least one transport element only for the ligature clip furthest forward adjacent to the discharge end of the cartridge.

18. Cartridge according to claim 10, wherein the holding projections on the at least one transport element and/or on the retaining element are configured as pivoted-out tongues which are separated out of a plane of the at least one transport element and/or the retaining element by a C-shaped dividing line and which can be pivoted elastically into the plane of the at least one transport element and/or the retaining element.

19. Cartridge according to claim 10, wherein the holding projections on the at least one transport element are arms lying in a plane of the at least one transport element, which protrude upwards and/or downwards from a longitudinal edge and can be pivoted elastically in towards an opposite longitudinal edge of the at least one transport element, and which arms in a pivoted-out state pass from an inside outwards through the space between the adjacent sections of the legs of the ligature clips and in the pivoted-out state abut against a connection of the adjacent sections of the ligature clip at the free end of the legs.

20. Cartridge according to claim 19, wherein in the pivoted-out state the arms are guided outside the legs of the ligature clips in a longitudinal guide means of the housing.

21. Cartridge according to claim 10, wherein in place of the elastically deformable holding projections on the at least one transport element and/or the retaining element, non-deformable holding projections are provided, which lie in a plane of the at least one transport element and/or the retaining element and protrude upwards and/or downwards from a longitudinal edge, and which on one side have a slide surface, on which the ligature clips can slide with elastic expansion past the holding projection, whereas on an opposite side they have an abutment surface, which abuts against the ligature clip and prevents the ligature clip from sliding past the holding projection.

22. Cartridge according to claim 21, wherein the holding projection has a form of a saw tooth.

23. Cartridge according to claim 1, wherein a feed member follows the last ligature clip of the row and is displaced in a direction of advance in the same manner as the ligature clips.

24. Cartridge according to claim 23, wherein the feed member advances the last ligature clip and ligature clips arranged in front of this the last ligature clip and in contact with the respective adjacent ligature clip in the direction of advance.

25. Cartridge according to claim 24, wherein the feed member is resiliently-biased in the direction of advance.

26. Cartridge according to claim 23, wherein the feed member has an inner space, into which the at least one transport element enters in a guided manner when the feed member advances, so that the feed member guides the at least one transport element in a region in which the at least one transport element had previously been guided by ligature clips.

27. Cartridge according to claim 1, wherein:
the at least one transport element comprises a first transport element and a second transport element arranged in the space between the adjacent sections of the ligature clips so that the first transport element and the second transport element can be slid forward and back relative to the housing, and
the second transport element effects the advance of the ligature clip furthest forward and the first transport element effects the stepwise advance of all following ligature clips.

28. Cartridge according to claim 27, wherein the first transport element and the second transport element are configured as flat strips abutting flat against one another.

29. Cartridge according to claim 28, wherein one of the first and the second transport elements has a longitudinal groove, in which the other transport element is received in a guided manner.

30. Cartridge according to claim 1, wherein for sliding the at least one transport element forward and back, a slide is disposed on the housing so that it can be slid forward and back in a direction of advance, said slide being connected to the at least one transport element by means of intermeshing projections and recesses, so that the slide entrains the at least one transport element at least during a portion of its sliding movement.

31. Cartridge according to claim 30, wherein:
the at least one transport element comprises a first transport element and a second transport element, and
the slide is in an entrainment connection with the first and second transport elements, whereby the slide entrains the first transport element and the second transport element over different portions of its own sliding movement.

32. Cartridge according to claim 31, wherein:
the first transport element, which effects a stepwise advance of all ligature clips with the exception of the one furthest forward, is entrained only over a portion of the sliding movement of the slide,
the second transport element, which displaces the ligature clip furthest forward to at least the discharge end of the cartridge, is entrained over an entire sliding movement of the slide.

33. Cartridge according to claim 32, wherein the slide engages by means of a projection into a recess of the first transport element, the recess in a displacement direction being longer than the projection and shorter than the sliding movement of the slide.

34. Cartridge according to claim 33, wherein the slide engages by means of a projection into a recess of the second transport element, the recess in a displacement direction being equal in length to the projection.

35. Cartridge according to claim 30, wherein an entrainment connection between the slide and the at least one transport element is arranged along the at least one transport element so that during the forward and/or return movement the at least one transport element is under tension at least in a portion of a longitudinal extent and not under compression.

36. Cartridge according to claim 35, wherein a first entrainment connection for the advance in a direction of the discharge end of the cartridge and a second entrainment connection for the opposed return movement are provided between the slide and the at least one transport element, and the first entrainment connection lies closer to the discharge end than the second entrainment connection.

37. Cartridge according to claim 36, wherein the entrainment connection adjacent to the discharge end of the cartridge comprises an elastically deformable entrainment means, which can slide elastically past a ligature clip located behind the slide during the return movement thereof.

38. Cartridge according to claim 1, wherein in the case of the ligature clip furthest forward in the row, the at least one transport element projects into the space between the two adjacent sections.

39. Cartridge according to claim 1, further comprising clamping elements at the discharge end of the cartridge, which during discharge and/or after discharge from the cartridge secure the ligature clip furthest forward against displacement along the row.

40. Cartridge according to claim 39, wherein the clamping elements are formed by the clamping jaws, which adjoin the cartridge in a direction of advance, between which the ligature clip furthest forward is inserted after discharging from the cartridge and a spacing of which is dimensioned so that the legs of the ligature clip are bent towards one another.

41. Cartridge according to claim 39, wherein the clamping elements are holding members, which are arranged on the cartridge and penetrate into a feed path of the ligature clip furthest forward, abut against the ligature clip furthest forward when sliding past and are thus elastically removable thereby out of the feed path.

* * * * *

UNITED STATES PATENT AND TRADEMARK OFFICE
CERTIFICATE OF CORRECTION

| | |
|---|---|
| PATENT NO. | : 8,585,718 B2 |
| APPLICATION NO. | : 13/218583 |
| DATED | : November 19, 2013 |
| INVENTOR(S) | : Alexander Disch et al. |

It is certified that error appears in the above-identified patent and that said Letters Patent is hereby corrected as shown below:

In the Claims:

Column 18, line 63, Claim 24: "arranged in front of this the last ligature clip and in contact" should read -- arranged in front of the last ligature clip and in contact --

Signed and Sealed this
Twenty-ninth Day of April, 2014

Michelle K. Lee
*Deputy Director of the United States Patent and Trademark Office*